(12) United States Patent
Jo et al.

(10) Patent No.: US 11,123,016 B2
(45) Date of Patent: Sep. 21, 2021

(54) PORTABLE BIO INFORMATION MEASURING DEVICE

(71) Applicant: Samsung Electronics Co., Ltd., Suwon-si (KR)

(72) Inventors: Seong-Wook Jo, Suwon-si (KR); Young-Hyun Kim, Suwon-si (KR); Jae-Hong Kim, Incheon (KR); Min-Hyoung Lee, Seongnam-si (KR); Jea-Hyuck Lee, Anyang-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 811 days.

(21) Appl. No.: 15/172,663

(22) Filed: Jun. 3, 2016

(65) Prior Publication Data

US 2016/0354036 A1 Dec. 8, 2016

(30) Foreign Application Priority Data

Jun. 4, 2015 (KR) ........................ 10-2015-0079227

(51) Int. Cl.
*A61B 5/00* (2006.01)
*A61B 5/0537* (2021.01)
*A61B 5/282* (2021.01)

(52) U.S. Cl.
CPC .......... *A61B 5/6898* (2013.01); *A61B 5/0022* (2013.01); *A61B 5/0537* (2013.01); *A61B 5/282* (2021.01); *A61B 2560/0468* (2013.01); *A61B 2562/0214* (2013.01); *A61B 2562/0285* (2013.01); *A61B 2562/166* (2013.01)

(58) Field of Classification Search
CPC . A61B 5/0022; A61B 5/6898; A61B 5/04085; A61B 5/0537; A61B 2560/0468; A61B 2562/0214; A61B 2562/0285; A61B 2562/166
See application file for complete search history.

(56) References Cited

U.S. PATENT DOCUMENTS

| | | | |
|---|---|---|---|
| 8,573,984 B2 | 11/2013 | Miller | |
| 8,587,533 B2 | 11/2013 | Nishihara et al. | |

(Continued)

FOREIGN PATENT DOCUMENTS

| | | |
|---|---|---|
| JP | 2011-194132 A | 10/2011 |
| KR | 10-2005-0105822 A | 11/2005 |

(Continued)

OTHER PUBLICATIONS

European Office Action dated Feb. 13, 2019; Application #: 16 803 785.1-1115; Ref #: P18324WOEP.

(Continued)

*Primary Examiner* — Eun Hwa Kim
*Assistant Examiner* — Adam Z Minchella
(74) *Attorney, Agent, or Firm* — Jefferson IP Law, LLP

(57) ABSTRACT

A portable bio information measuring device is provided. The portable bio information measuring device includes a circuit board placed in the portable bio information measuring device, a housing accommodating the circuit board, an electrode to measure bio information, and a connecting member electrically connecting the circuit board with the electrode. The electrode is configured as at least one of a transparent electrode, a conductive decoration, and a conductive printed electrode.

9 Claims, 34 Drawing Sheets

(56) References Cited

U.S. PATENT DOCUMENTS

| | | |
|---|---|---|
| 8,615,290 B2 | 12/2013 | Lin et al. |
| 9,445,740 B1* | 9/2016 | Crone .................... A61B 5/282 |
| 2004/0115614 A1 | 6/2004 | Burnett et al. |
| 2005/0239493 A1* | 10/2005 | Batkin ................. A61B 5/0404 |
| | | 455/550.1 |
| 2007/0021677 A1 | 1/2007 | Markel |
| 2007/0070476 A1 | 3/2007 | Yamada et al. |
| 2011/0015496 A1* | 1/2011 | Sherman ................ A61B 5/332 |
| | | 600/301 |
| 2011/0034786 A1 | 2/2011 | Cadio et al. |
| 2012/0022385 A1* | 1/2012 | Shimuta ................. A61B 5/332 |
| | | 600/509 |
| 2012/0092812 A1 | 4/2012 | Lewis et al. |
| 2012/0103777 A1 | 5/2012 | Kang |
| 2012/0136227 A1 | 5/2012 | McKenna |
| 2012/0265026 A1* | 10/2012 | Shenasa ............... A61B 5/0006 |
| | | 600/301 |
| 2012/0296231 A1 | 11/2012 | Osoegawa et al. |
| 2013/0005303 A1* | 1/2013 | Song ................. A61B 5/02438 |
| | | 455/411 |
| 2013/0005310 A1 | 1/2013 | Lim et al. |
| 2013/0215042 A1 | 8/2013 | Messerschmidt et al. |
| 2014/0042406 A1 | 2/2014 | Degner et al. |
| 2014/0107493 A1* | 4/2014 | Yuen .................... A61B 5/6898 |
| | | 600/473 |
| 2014/0120876 A1 | 5/2014 | Shen |
| 2014/0350362 A1 | 11/2014 | Raptis et al. |
| 2014/0362044 A1 | 12/2014 | Cho et al. |
| 2015/0185055 A1* | 7/2015 | King .................... G01D 11/245 |
| | | 361/679.01 |
| 2016/0296132 A1* | 10/2016 | Bojovic ................. A61B 5/684 |

FOREIGN PATENT DOCUMENTS

| | | |
|---|---|---|
| KR | 10-2011-0027113 A | 3/2011 |
| KR | 10-2012-0043883 A | 5/2012 |
| KR | 10-2012-0097219 A | 9/2012 |
| KR | 10-2013-0007117 A | 1/2013 |
| KR | 10-2014-0098652 A | 8/2014 |
| KR | 10-2014-0144552 A | 12/2014 |
| KR | 10-2015-0039505 A | 4/2015 |
| WO | 2011/022942 A1 | 3/2011 |

OTHER PUBLICATIONS

Korean Office Action with English translation dated Jun. 29, 2021; Korean Appln. No. 10-2015-0079227.

* cited by examiner

PORTABLE BIO INFORMATION MEASURING DEVICE

CROSS-REFERENCE TO RELATED APPLICATION(S)

This application claims the benefit under 35 U.S.C. § 119(a) of a Korean patent application filed on Jun. 4, 2015 in the Korean Intellectual Property Office and assigned Serial number 10-2015-0079227, the entire disclosure of which is hereby incorporated by reference.

TECHNICAL FIELD

The present disclosure relates to portable bio information measuring devices.

BACKGROUND

As more interest is attracted to health, users may measure or manage their health conditions by various medical devices. For example, a user may measure his bio signals including blood pressure, heartbeat, or pulse and continue to manage diseases such as high blood pressure or diabetes using the measured bio signals.

The presence of a ubiquitous environment under which various information is communicable via a free connection regardless of time or place would allow many users to share a diversity of information. Such a ubiquitous healthcare (U-healthcare) may provide medical services through a network even without visiting a doctor's office or hospital, and accordingly, various medical devices are being developed to utilize the same.

As such network environment stands and wearable electronic devices become commercially available, a convergent medical service attracts more attention. For example, an electronic device worn on a human body may measure, in real-time, the user's blood pressure, heartbeat, or pulse and transmit the measured result to another user's electronic device or medical organization through a network.

To detect the user's bio signals, the wearable electronic device may require a plurality of electrodes directly contacting the user's body. Such electrodes are exposed to the outside of the electronic device. The exposed electrodes may be an obstacle to allowing the electronic device a luxurious look and feel, as well as diversified designs. Further, when mounting a device for detecting bio signals in an electronic device with a touch input unit, interference may occur between the bio signal detecting device and the touch input unit of the electronic device or touch inputs may be hampered. Further, such electrodes requiring connecting parts, e.g., a conductive pad, a pogo pin, or c-clip, may render a compact electronic device to secure a space for installing the same.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below.

In accordance with an aspect of the present disclosure, an electronic device capable of detecting a user's bio signals, which have electrodes on an outer portion thereof without spoiling the appearance is provided.

In accordance with another aspect of the present disclosure, an electronic device is provided. The electronic device includes a metallic decoration, such as a metallic emblem or design, on an outer portion thereof, which may provide an electrical connection between an electrode and a circuit board, allowing for an aesthetic design of the electronic device and an electrical connection of the bio signal device.

In accordance with another aspect of the present disclosure, an easy-to-miniaturize electronic device that enables installation of electrodes for detecting bio signals in a narrow space is provided.

In accordance with another aspect of the present disclosure, a portable bio information measuring device is provided. The device includes a circuit board placed in the portable bio information measuring device, a housing accommodating the circuit board, an electrode configured as at least one of a transparent electrode, a conductive decoration, or a conductive printed electrode to measure bio information, and a connecting member electrically connecting the circuit board with the electrode.

In accordance with another aspect of the present disclosure, a portable bio information measuring device is provided. The device includes a cover unit covering at least a surface of the device and separable from the device, an electrode configured as one of a transparent electrode, a conductive decoration, or a conductive printed electrode in the cover unit to measure bio information, and a connecting member electrically connecting the electrode to the device as the cover unit couples.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
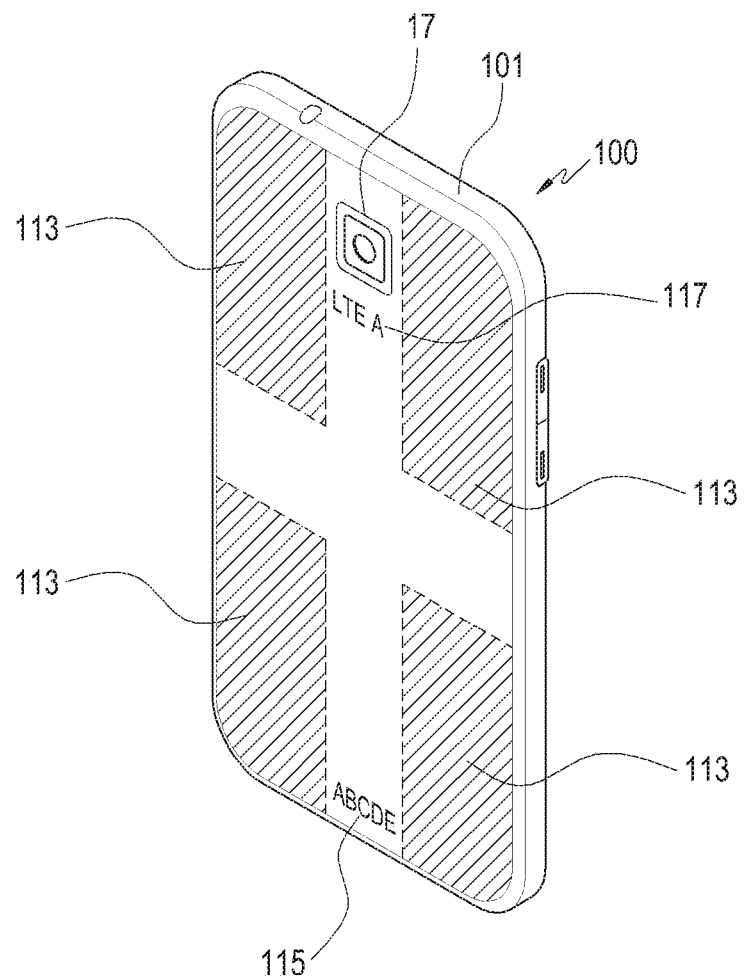
FIG. 1 is a rear perspective view schematically illustrating a portable bio information measuring device according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

The terms coming with ordinal numbers such as 'first' and 'second' may be used to denote various components, but the components are not limited by the terms. The terms are used only to distinguish one component from another. For example, a first component may be denoted a second component, and vice versa without departing from the scope of the present disclosure. The term "and/or" may denote a combination(s) of a plurality of related items as listed or any of the items.

The terms "front," "rear surface," "upper surface," and "lower surface" are relative ones that may be varied depending on directions in which the figures are viewed, and may be replaced with ordinal numbers such as "first" and "second." The order denoted by the ordinal numbers, first and second, may be varied as necessary.

The terms as used herein are provided merely to describe some embodiments thereof, but not to limit the present disclosure. It is to be understood that the singular forms "a," "an," and "the" include plural references unless the context clearly dictates otherwise. Thus, for example, reference to "a component surface" includes reference to one or more of such surfaces. It will be further understood that the terms "comprise" and/or "have," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which the embodiments of the present disclosure belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the term "electronic device" may be any device with a touch panel, and the electronic device may also be referred to as a terminal, a portable terminal, a mobile terminal, a communication terminal, a portable communication terminal, a portable mobile terminal, or a display apparatus.

For example, the electronic device may be a smartphone, a mobile phone, a navigation device, a game device, a TV, a head unit for vehicles, a laptop computer, a tablet computer, a personal media player (PMP), or a personal digital assistant (PDA). The electronic device may be implemented as a pocket-sized portable communication terminal with a radio communication function. According to an embodiment of the present disclosure, the electronic device may be a flexible device or a flexible display.

The electronic device may communicate with an external electronic device, e.g., a server, or may perform tasks by interworking with such an external electronic device. For example, the electronic device may transmit an image captured by a camera and/or location information detected by a sensor to a server through a network. The network may include, but is not limited to, a mobile or cellular communication network, a local area network (LAN), a wireless local area network (WLAN), a wide area network (WAN), the Internet, or a small area network (SAN).

In describing various embodiments of the present disclosure, there are disclosed examples in which electrodes 113 for detecting bio signals are formed on a rear and front surface of an electronic device portable bio information measuring device 100 (hereinafter, a housing 101). The present disclosure is not limited to such embodiments, and the electrodes 113 for detecting bio signals may be formed on either or both of the rear and front surface of the electronic device portable bio information measuring device 100 (e.g., the housing 101). Further, when the electrodes 113 are formed on both the rear and front surface of the electronic device portable bio information measuring device 100, the following embodiments may be implemented in a combination thereof.

Figure 2:
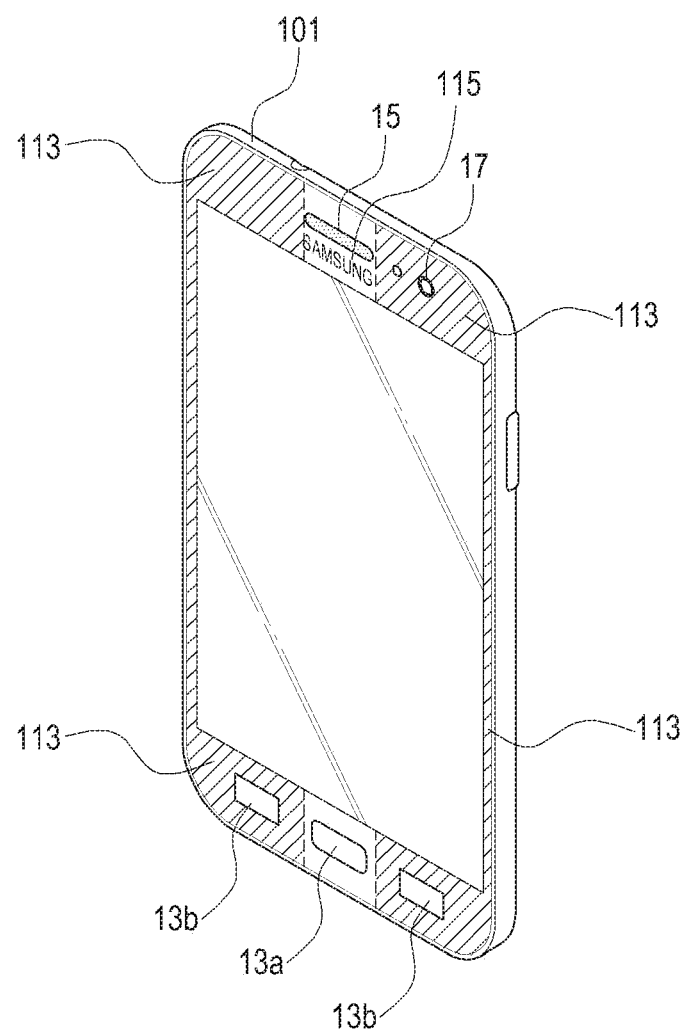
FIG. 2 is a front perspective view schematically illustrating a portable bio information measuring device according to an embodiment of the present disclosure.

FIG. 1 is a rear perspective view schematically illustrating a portable bio information measuring device 100 according to an embodiment of the present disclosure. FIG. 2 is a front perspective view schematically illustrating a portable bio information measuring device 100 according to an embodiment of the present disclosure.

Referring to FIGS. 1 and 2, the portable bio information measuring device 100 may include a circuit board 19 (identified in at least FIGS. 21-23), a housing 101, an input unit 11 (identified in at least FIGS. 26, 28, 29, 31, 33, 34, 36B, 37B and 38), electrodes 113 (as described below, the electrodes 113 may include transparent electrodes and conductive printed electrodes), and connecting members 111 (identified in at least FIGS. 3, 4, 6, 8-11 and 17-26).

The circuit board 19 is a structure received in the housing 101. Various integrated circuit chips such as an application processor, memory, or communication module may be mounted on the circuit board 19. Further, the electrodes 113 for detecting bio signals described below may be electrically connected with the circuit board 19 in various manner.

The housing 101 may form an outer appearance of the portable bio information measuring device 100, and various components, such as a bracket 21 (refer to, e.g., FIG. 15) or circuit board 19 (refer to, e.g., FIG. 15) may be placed inside the housing 101. Further, at least a surface of the housing 101, specifically a front surface of the housing 101, may have a device capable of displaying screen or implementing an input, e.g., an input unit 11 including a display unit (not shown) such as a liquid crystal display (LCD) or touch panel (not shown), a keypad or a receiving part. Another surface of the housing 101, specifically a rear surface of the housing 101, may include a camera module 17 or fingerprint recognition device 15 or other modules installed thereon. The keypad may include a button 13a operated by mechanical manipulation and a touch key 13b operated by the user's body contact. Although mentioned above, the input unit 11 may be equipped with a touch panel to output screen, and the input unit 11 may also be used as an input device.

As mentioned above, the input unit 11 may be provided in at least one surface of the housing 101 to implement a touch input. According to an embodiment of the present disclosure, the input unit 11 may be, e.g., a large-size display apparatus including a touch panel and a display unit. Thus, the input unit 11 may be utilized as an input device as well as outputs screen. However, the configuration of the input unit 11 is not limited thereto.

According to an embodiment of the present disclosure, one or more pairs of electrodes 113 may be provided in the housing 101 or cover unit 200 covering the housing 101 to detect the user's bio signals. The electrodes 113 may have various structures, shapes or configurations. For example, the electrodes 113 according to the present disclosure may be arranged as transparent electrodes 113 on an outer surface of the housing 101, otherwise as conductive printed electrodes 113 on the outer surface of the housing 101, or otherwise arranged using a conductive decoration 117 provided in the housing 101.

When the electrodes 113 are provided as transparent electrodes 113, they may be arranged without influencing the look or design of the housing 101. By contrast, when the electrodes 113 are provided as conductive printed electrodes 113, a design, such as a regular or irregular pattern, may be formed on the outer surface of the housing 101. Further, when the electrodes 113 are provided as a conductive decoration 117, various logos, patterns, letters, or shapes may be mounted or arranged on the outer surface of the housing 101 and may be simultaneously utilized as electrodes 113 able to measure bio information.

Further, the electrodes 113 may be directly formed on the outer surface of the housing 101 or cover unit 200 (refer to FIG. 33) or may be implemented so that they are formed on the transparent film or base substrate 150 (refer to FIG. 14) formed of glass or synthetic resin and coupled with the housing 101 or the cover unit 200. Further, the electrodes 113 may be formed by depositing or plating a conductive material on the outer surface of the housing 101 or cover unit 200 or a transparent film or base substrate that may be provided on the outer surface of the housing 101 or the cover unit 200.

Figure 3:
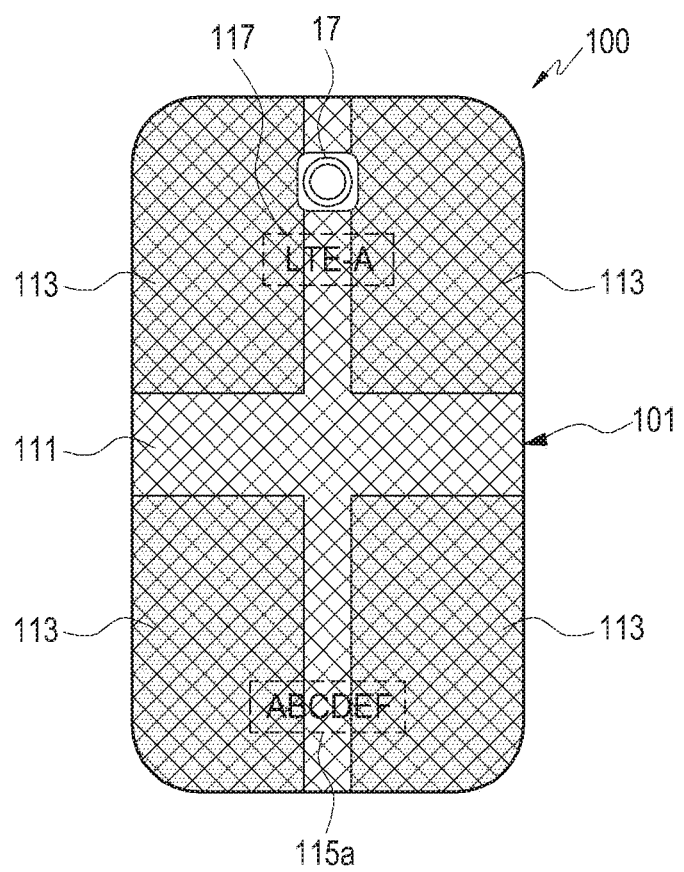
FIG. 3 is a view illustrating a portable bio information measuring device according to an embodiment of the present disclosure.

With reference to FIG. 3, the connecting member 111 is a component that electrically connects the electrodes 113 to the housing 101, specifically, the circuit board 19 implemented inside the housing 101. The connecting member 111 may have various embodiments depending on the structure of the electrodes 113 (e.g., 111e, 111f, 111h, 111i, 111j, and so forth). For example, the connecting member 111 may be formed as a via hole 111e between the electrode 113 and the circuit board 19, formed of conductive decoration 117 implemented on the outer surface of the housing 101 and electrically connected with the circuit board 19 via the conductive decoration 117, formed of decorative metal frames 31a, 31b, and 31c surrounding various modules provided in the housing 101 to be electrically connected with the circuit board 19 via the metal frames 31a, 31b, and 31c of the modules, or formed of frames 31a, 31b, and 31c provided on the side of the edge of the housing 101 to be electrically connected with the circuit board 19 via the side frames 31a, 31b, and 31c of the housing 101. Further, the connecting member 111 may be implemented as at least one of a conductive ink, a flexible printed circuit board, and a conductive mesh and may be formed of the same or different material from the electrodes 113. The above-described embodiments may be excluded from a specific description of the portable bio information measuring device 100 described below.

Hereinafter, common features or configurations of the portable bio information measuring devices 100 are described first, followed by a description of the differences.

As set forth above, the electrodes 113 may be implemented as transparent electrodes 113 on the outer surface of the housing 101 or the cover unit 200, as conductive printed electrodes 113, or conductive decoration 117.

An example of arranging electrodes 113 on the outer surface of the housing 101 is described with reference to FIGS. 3 to 10.

Figure 4:
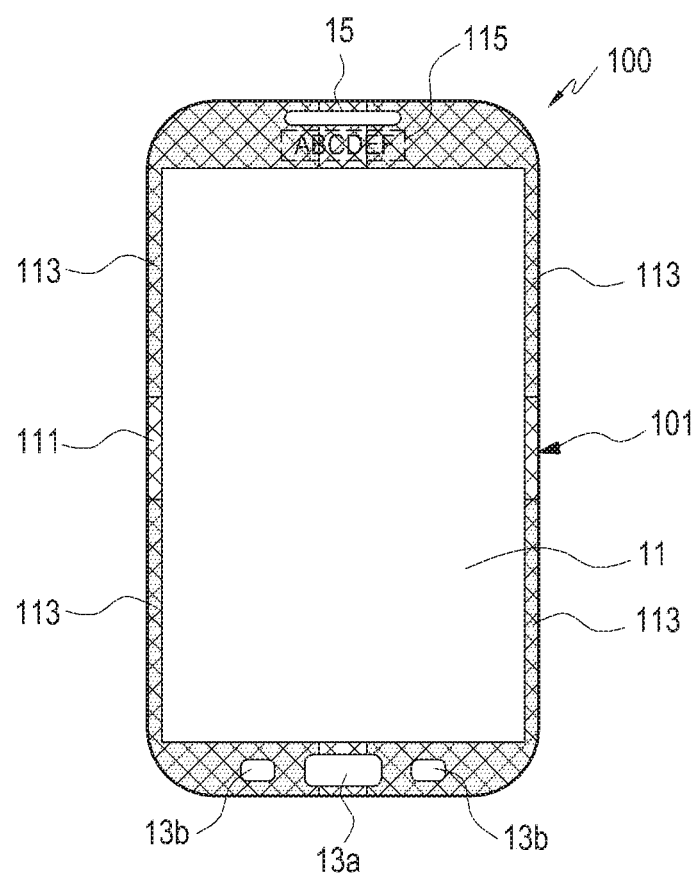
FIG. 4 is a view illustrating a portable bio information measuring device according to an embodiment of the present disclosure.
Figure 5:
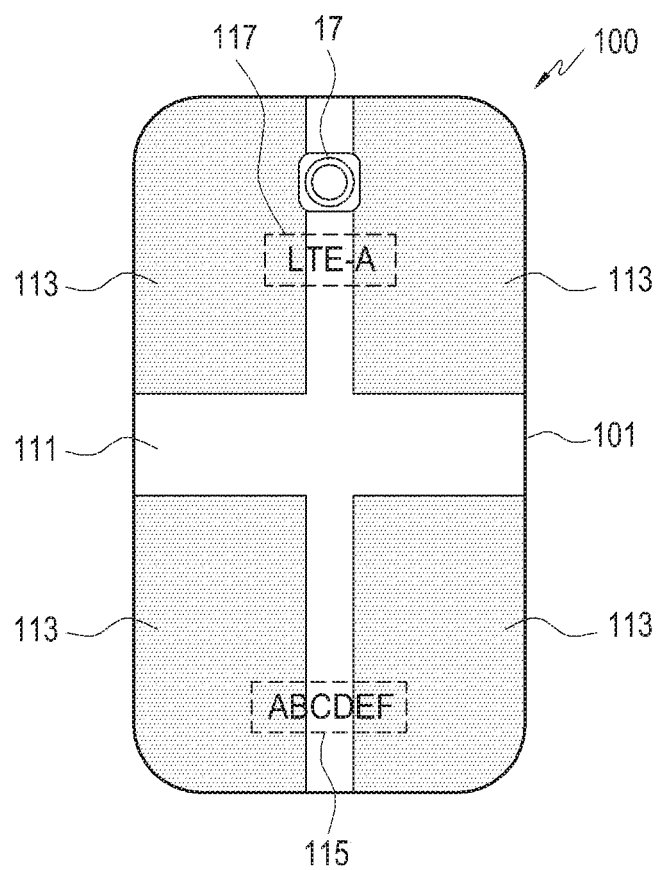
FIG. 5 is a view illustrating an embodiment of the present disclosure.
Figure 6:
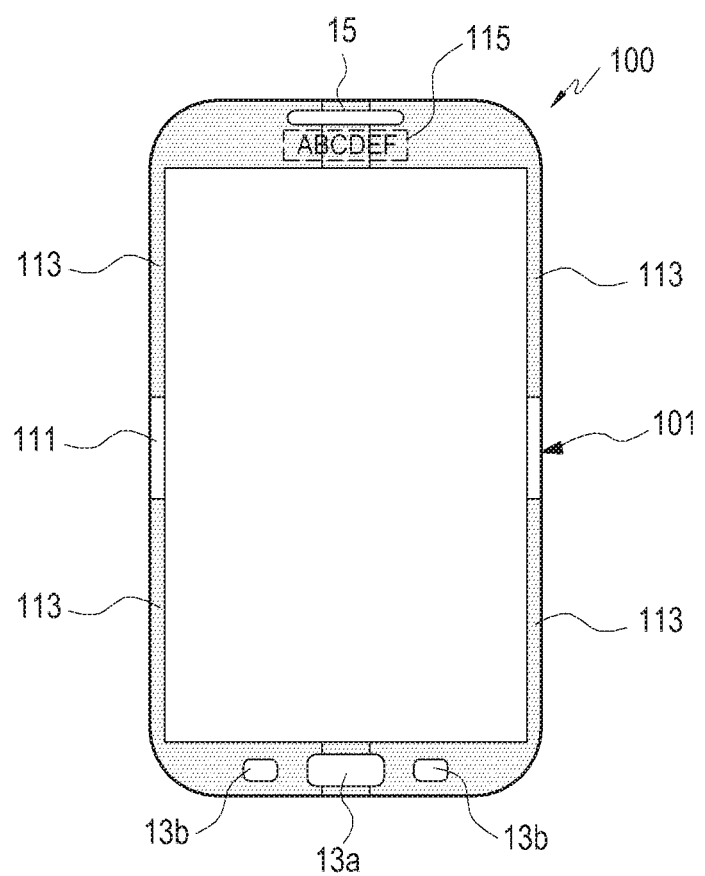
FIG. 6 is a view illustrating a portable bio information measuring device according to an embodiment of the present disclosure.
Figure 7:
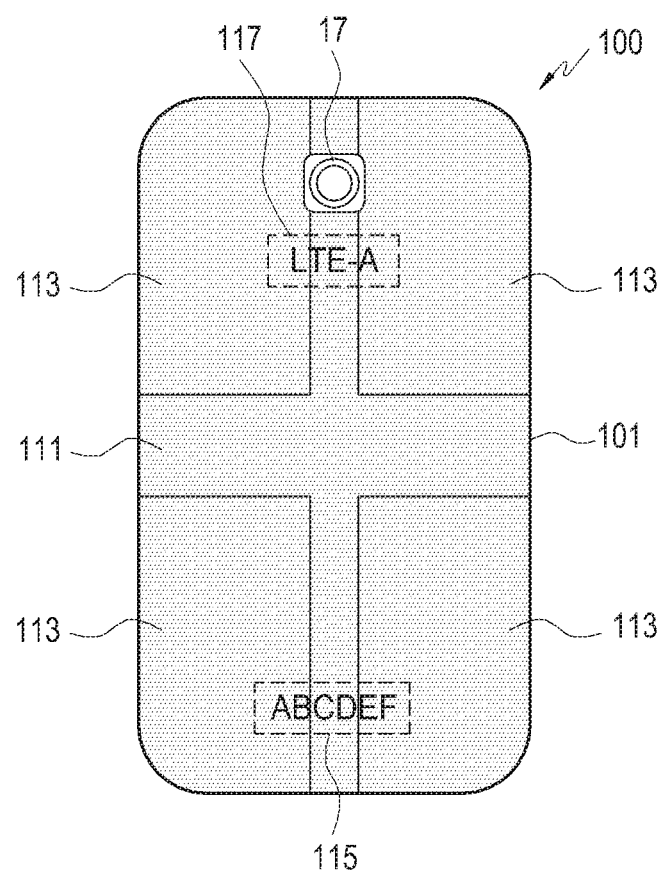
FIG. 7 is a view illustrating a portable bio information measuring device according to an embodiment of the present disclosure.
Figure 8:
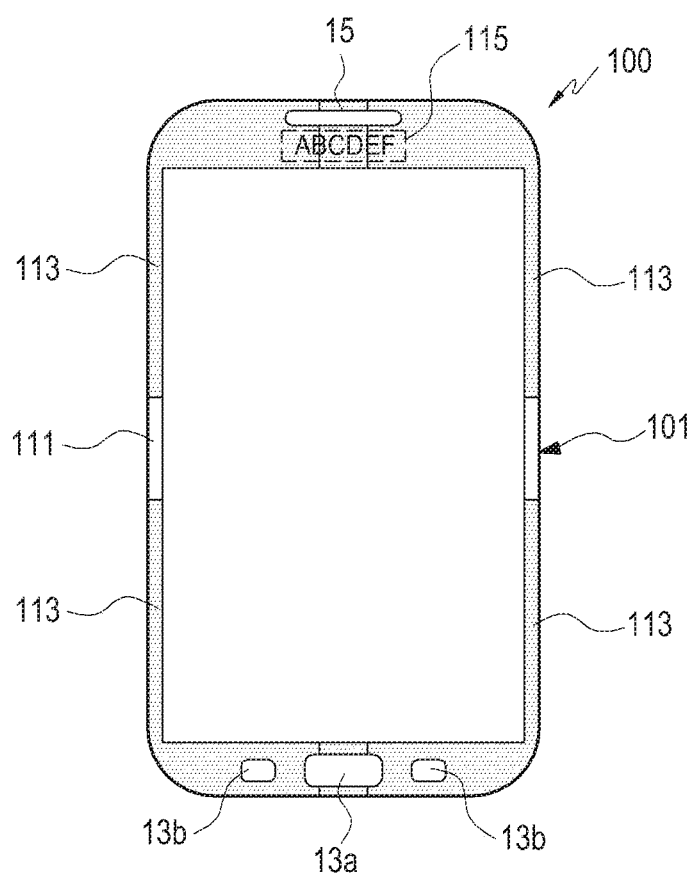
FIG. 8 is a view illustrating a portable bio information measuring device according to an embodiment of the present disclosure.
Figure 9:
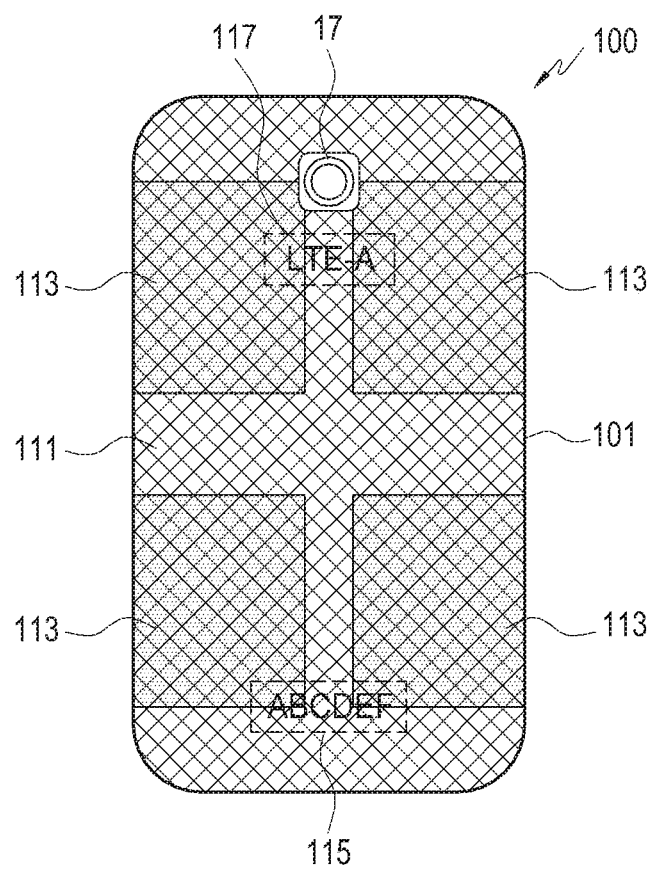
FIG. 9 is a view illustrating a portable bio information measuring device according to an embodiment of the present disclosure.
Figure 10:
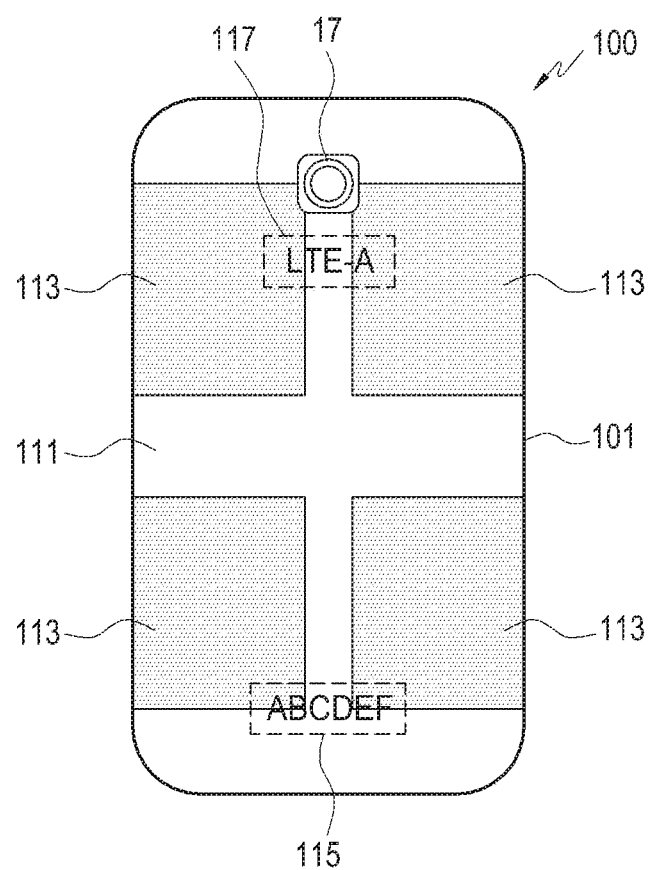
FIG. 10 is a view illustrating a portable bio information measuring device according to an embodiment of the present disclosure.

FIG. 3 is a view illustrating a portable bio information measuring device 100 according to an embodiment of the present disclosure. FIG. 4 is a view illustrating a portable bio information measuring device 100 according to an embodiment of the present disclosure. FIG. 5 is a view illustrating an embodiment of the present disclosure. FIG. 6 is a view illustrating a portable bio information measuring device 100 according to an embodiment of the present disclosure. FIG. 7 is a view illustrating a portable bio information measuring device 100 according to an embodiment of the present disclosure. FIG. 8 is a view illustrating a portable bio information measuring device 100 according to an embodiment of the present disclosure. FIG. 9 is a view illustrating a portable bio information measuring device 100 according to an embodiment of the present disclosure. FIG. 10 is a view illustrating a portable bio information measuring device 100 according to an embodiment of the present disclosure.

FIGS. 1, 3, 5, 7, and 9 are views illustrating an example in which electrodes 113, e.g., transparent electrodes 113 or conductive printed electrodes 113, are provided on the rear surface of the housing 101, and FIGS. 2, 4, 6, 8, and 10 are views illustrating an example in which electrodes 113, e.g., transparent electrodes 113 or conductive printed electrodes 113, are provided on the front surface of the housing 101.

Referring to FIGS. 3 to 10, two pairs of electrodes 113 for detecting bio signals may be arranged on the rear surface of the portable bio information measuring device 100, specifically, on the rear surface of the housing 101. When detecting bio signals, different bio signals may be detected according to a combination of a plurality of electrodes 113 contacted by the user. For example, when the user's body contacts first and second electrodes of the electrodes 113, a body fat index may be detected, and when the user's body contacts a plurality of electrodes, such as the first, second, and third electrodes, an electrocardiogram (ECG) may be detected.

The electrodes 113 may be formed of transparent electrodes 113 or conductive printed electrodes 113 formed on the rear surface of the portable bio information measuring device 100, e.g., the rear surface of the housing 101. When the electrodes 113 are formed of transparent electrodes 113, the degree of freedom in designing, e.g., the color or pattern of the outer appearance of the housing 101 may be enhanced. When the electrodes 113 are formed of transparent electrodes 113, the transparent electrodes 113 may include at least one of an indium tin oxide, a conductive mesh, silver nano, or graphene. When the electrodes 113 are formed of conductive printed electrodes 113, the electrodes 113 may include at least one of conductive printed layers 115 and 117, a conductive mesh, or a metal member. For example, patterns regularly or irregularly repeated may be formed on the whole rear surface, or a predetermined pattern or design may be formed at a predetermined position on the rear surface. When the electrodes 113 are formed of the conductive decoration 117, they may include at least one of conductive printed layers 115 and 117, a conductive mesh or metal member, or metal frames 31a, 31b, and 31c, and such materials may form various designs or patterns or outer frames 31a, 31b, and 31c on the outer surface of the housing 101.

The connecting member 111 may be provided between the electrodes 113 and the circuit board 19 to connect the electrodes 113 to a circuit device (e.g., the circuit board 19) placed inside the housing 101. Such connecting member 111 may be implemented independently in material or structure from the electrodes 113, and the connecting member 111 and the electrodes 113 may be formed of the same or different materials. For example, the electrodes 113 and the connecting members 111 all may be formed of conductive meshes. By contrast, the electrodes 113 may be formed of indium tin oxide while the connecting members 111 may be formed of conductive mesh, silver nano, or graphene. However, the electrodes 113 or connecting member 111 may be implemented variously considering the freedom of design for the color of outer appearance of the housing 101.

For example, as shown in FIG. 3 or 4, in the portable bio information measuring device 100, the electrodes 113 may be provided as a mesh shape of transparent electrodes 113 or conductive printed electrodes 113 on the front or rear surfaces of the housing 101. Further, in the case shown in FIG. 3 or 4, the connecting members 111 are arranged in a conductive mesh shape under the mesh-shaped electrodes 113 to be connected with the circuit board 19 inside the housing 101.

As shown in FIG. 5 or 6, in the portable bio information measuring device 100, the electrodes 113 may be provided as transparent electrodes 113 or conductive printed electrodes 113 formed as regular or irregular pattern or printed layer 117 on the front or rear surface of the housing 101. Accordingly, when the electrodes 113 are implemented as transparent electrodes 113, the electrodes 113, although shown to be exposed in FIGS. 5 and 6, may be provided in two pairs in the housing 101 while not visually exposed. In contrast, when the electrodes 113 are implemented as conductive printed electrodes 113, the electrodes 113 may be provided in two pairs in the housing 101 while exposed to the outer surface of the housing 101 as shown in FIG. 5 or 6. Further, in the case shown in FIG. 5 or 6, as the electrodes 113 are arranged at a lower portion of the electrodes 113 to be connected with the circuit board 19 provided inside the housing 101 and implemented of a transparent material, e.g., indium tin oxide, the electrodes 113 may be provided to connect with the circuit board 19 without visual exposure in the outer surface of the housing 101.

Further, in the portable bio information measuring device 100 according to various embodiments of the present disclosure, as shown in FIG. 7 or 8, the electrodes 113 may be formed of transparent electrodes 113 so that a visual decoration having the regular or irregular patterns or designs repeatedly formed on the outer surface of the housing 101 may be externally exposed. The connecting member 111 may be formed of transparent electrodes 113 so that a visual decoration having the regular or irregular patterns or designs repeatedly formed on the outer surface of the housing 101 may be externally exposed. Such electrodes 113 or connecting member 111 may be implemented by surface-treating, coating or printing the housing 101.

By contrast, the electrodes 113 may be formed of a visual decoration having regular or irregular patterns or predetermined designs repeatedly formed on the front or rear surface of the housing 101. Further, the connecting member 111 may be arranged at a lower portion of the electrodes 113 to connect the electrodes 113 to the circuit board 19 provided inside the housing 101 and may be formed of a visual decoration having regular or irregular patterns or predetermined designs repeated formed to engage with the patterns of the electrodes 113. Such electrodes 113 or connecting member 111 may be implemented by surface-treating, coating or printing the housing 101.

For example, as implemented of indium tin oxide, the electrodes 113 may be provided to connect with the circuit board 19 while not visually exposed in the outer surface of the housing 101.

Further, in the portable bio information measuring device 100 illustrated in FIG. 9 or 10, the electrodes 113 and the connecting member 111 may be positioned on the rear or front surface of the housing 101 with the same structure or shape as those in the prior embodiments, and the area where the electrodes 113 are arranged may be partially adjusted. For example, when an antenna device is disposed inside the housing 101, the position where the electrodes 113 having the structure or configuration described above in connection with the prior embodiments are placed or formed may be further shrunken or may be provided avoiding the installation area of the antenna device to allow the antenna device a stable performance. The electrodes 113, as a conductive material, may have the property of absorbing or shielding radio waves radiated from the antenna device. A lowering in performance of the antenna device may be prevented due to the electrodes 113 by shrinking the installation area of the electrodes 113g and 113h or arranging them in an area other than where the antenna device is disposed.

As described above in connection with FIGS. 1 to 10, according to an embodiment of the present disclosure, the portable bio information measuring device 100 may include a plurality of electrodes 113 formed on the rear or front surface of the housing 101. The electrodes 113 may contact the user's body to detect bio information, e.g., ECG or body fat index. When the user's body contacts a pair of electrodes or more to detect bio signals, in case three or more electrodes 113 are arranged, different bio signals may be detected depending on combinations of electrodes 113 contacted by the user. According to an embodiment of the present disclosure, when the logo of manufacturer or carrier or various designs are printed on the outer surface of the portable bio information measuring device 100, the above-described electrodes 113 may be implemented by forming the printed layer 117 with a conductive material, e.g., a conductive ink or metal.

According to an embodiment of the present disclosure, the portable bio information measuring device 100 may include connecting members 111 for connecting the electrodes 113 to a circuit device. In the above-described embodiments, although the connecting members 111 are not specifically shown, it may be apparent to one of ordinary skill in the art that the connecting members 111 are formed or arranged to respectively correspond to the electrodes 113 in a one-to-one correspondence. The connecting members 111 may be formed of regularly or irregularly repeated patterns on the outer surface of the portable bio information measuring device 100 to provide a decorative effect to the outer appearance of the portable bio information measuring device 100.

The electrodes 1 and connecting members 111 connecting the electrodes 113 to the circuit board are now described according to an embodiment of the present disclosure.

As mentioned above, according to an embodiment of the present disclosure, the electrodes 113 may be provided as transparent electrodes 113, conductive printed electrodes 113, or conductive decoration 117.

For example, according to an embodiment of the present disclosure, the electrodes 113 may be formed of transparent electrodes 113 formed on the rear surface of the portable bio information measuring device 100, e.g., the rear surface of the housing 101. The transparent electrodes 113 for forming the electrodes 113 may include at least one of an indium tix oxide, silver nano, graphene, or a conductive mesh (also referred to as a "metal mesh"). Further, according to an embodiment of the present disclosure, the transparent electrodes 113 may be shaped to have a mesh pattern (refer to FIG. 3 or 4). When the electrodes 113 are formed as transparent electrodes 113 of one of the above-enumerated materials, the electrodes 113 may be formed on the outer surface of the housing 101, with the decoration of predetermined shapes, designs or patterns repeatedly formed on the outer surface of the housing 101 exposed to the outside. When the electrodes 113 are formed in mesh patterns of one of the above materials, the mesh patterns forming the electrodes 113 may be formed to be transparent so that they are invisible although they are shown as if they are visible in FIG. 3 or 4, and thus, the unique color of the housing 101 may be exposed to the outside even when the electrodes 113 or connecting members 111 are arranged on the outer surface, e.g., front or rear surface, of the housing 101.

Further, the housing 101 may include the connecting member 111 to connect the transparent electrode 113 to the circuit device of the portable bio information measuring device 100.

The connecting member 111 may be disposed between the transparent electrodes 113 and the outer surface of the housing 101 to connect the transparent electrodes 113 with the circuit board 19. For example, a grid-type conductive pattern may be disposed at a lower portion of the transparent electrodes 113 to connect the transparent electrodes 113 to the circuit board 19. The conductive pattern may be formed of the same or different material from the transparent electrodes 113. That is, when formed of the same material as the transparent electrodes 113, the connecting member 111 may also be formed to be transparent so that it is invisible. That is, as the electrodes 113 and the connecting member 111 are provided to be transparent on the outer surface of the housing 101, the color or design of the housing 101 may be exposed.

By contrast, the connecting member 111 may be formed of conductive printed layers 115 and 117 formed on the outer surface of the housing 101. The conductive printed layers 115 and 117 may form regular or irregular patterns and may include a decorative pattern making the appearance of the housing 101 look elegant. For example, the conductive printed layer 117 may be formed to provide a decorative design of regularly or irregularly repeated patterns or the symbol of manufacturer or carrier.

According to an embodiment of the present disclosure, although an example has been described in which the connecting member 111 is disposed between the transparent electrodes 113 and the housing 101 to be connected with the circuit board 19 disposed inside the housing 101 or may be implemented of conductive printed layers 115 and 117, the present disclosure is not limited thereto. Various changes or modifications may be made thereto in structure or configuration thereof, such as, e.g., the connecting member 111 implemented as a via hole 111e or as connecting terminals 111a and 111b. The connecting member 111 is described below in more detail.

Although an example has been described in which the electrodes 113 are transparent electrodes 113, the electrodes 113 may also be formed of conductive printed electrodes 113, not the transparent electrodes 113, according to an embodiment of the present disclosure. For example, according to an embodiment of the present disclosure, the electrodes 113 may be implemented of conductive printed electrodes 113 having regular or irregular mesh patterns. When the electrodes 113 are provided as conductive printed electrodes 113 having the mesh patterns, each pattern may be visually exposed to the outside of the housing 101. For example, the conductive printed electrodes 113 may be visually exposed with regular or irregular patterns on the outer surface of the housing 101, and the conductive printed electrodes 113 may form various designs on the outer surface of the housing 101 according to the patterns. According to an embodiment of the present disclosure, although an example is described in which the conductive printed electrodes 113 are rectangular and neighbor each other or implemented in a bezel area around the input unit 11, the present disclosure is not limited thereto. For example, the conductive printed electrodes 113 may be provided to have a separate design, e.g., a predetermined drawing, allowing the housing 101 various designs.

Further, a connecting member 111 may be formed to connect the conductive printed electrodes 113 to the circuit board 19 provided inside the housing 101.

The connecting member 111 may be formed of the same or different material from the conductive printed electrodes 113. The connecting member 111 may be formed in a number of connecting manners, e.g., via hole 111e, separate connecting terminals 111a and 111b, and the conductive printed electrodes 113 may be visually exposed to the outer surface of the housing 101. Thus, the connecting member 111 may be formed corresponding to the patterns or design of the conductive printed electrodes 113. For example, when the connecting member 111 is formed of the same material as the conductive printed electrodes 113, it may be formed corresponding to the patterns or design of the conductive printed electrodes 113. For example, when the connecting member 111 is formed of the same or different material (e.g., a transparent conductive mesh) from the conductive printed electrodes 113 and positioned at a lower portion of the conductive printed electrodes 113, the connecting member 111 may connect the conductive printed electrodes 113 to the circuit board 19 while not exposed from the appearance of the housing 101. Further, the connecting member 111 may be provided as a conductive decoration 117 on the outer surface of the housing 101. The connecting member 111 may be formed of the conductive decoration 117, e.g., he conductive printed layer 117 providing a decorative design of regularly or irregularly repeated patterns or the symbol of manufacturer or carrier.

According to an embodiment of the present disclosure, although an example is described in which the connecting member 111 is formed between the housing 101 and the conductive printed electrodes 113 or formed of the conductive decoration 117, the present disclosure is not limited thereto. Various changes or modifications may be made thereto in structure, configuration, or connection thereof, such as, e.g., the connecting member 111 implemented as the via hole 111e or the connecting terminals 111a and 111b. A specific configuration of the connecting member 111 is described below in more detail.

Further, although not shown, when the electrodes 113 are provided as conductive printed electrodes 113, dummy patterns may be provided between the conductive printed electrodes 113 spaced apart from each other to give more beauty to the outer design of the housing 101. For example, the conductive printed electrodes 113 are exposed as a visual decoration having patterns or designs regularly or irregularly repeated on the outer surface of the housing 101, and the shape of the outer surface of the housing 101 is exposed therebetween. Since the outer surface of the housing 101 differs between where the conductive printed electrodes 113 are arranged and where the conductive printed electrodes 113 are not, dummy patterns having consistent shapes or patterns may be provided to where the conductive printed electrodes 113 are not arranged to make the differences consistent in light of design. For example, when the conductive printed electrodes 113 are formed of a mesh pattern, the dummy patterns may also be formed of the same mesh pattern as the conductive printed electrodes 113 to be shown as if the same mesh pattern is formed on the entire surface of the housing 101.

Although an example has been described above in which the dummy patterns are formed where no conductive printed electrodes 113 are arranged, when the connecting member 111 is disposed under the conductive printed electrodes 113 to connect with the circuit board 19 inside the housing 101, the connecting member 111 may be provided to have the same or different pattern from the conductive printed electrodes 113 to form an outer design of the outer surface of the housing 101, instead of the dummy patterns. For example, when the conductive printed electrodes 113 on the outer surface of the housing 101 are provided on the outer surface to have grid-type patterns, the connecting member 111 may be configured to arrange grid-type conductive patterns on a lower surface of the conductive printed electrodes 113 so that the grid-type conductive patterns connect the conductive printed electrodes 113 with the circuit board 19.

Figure 11:
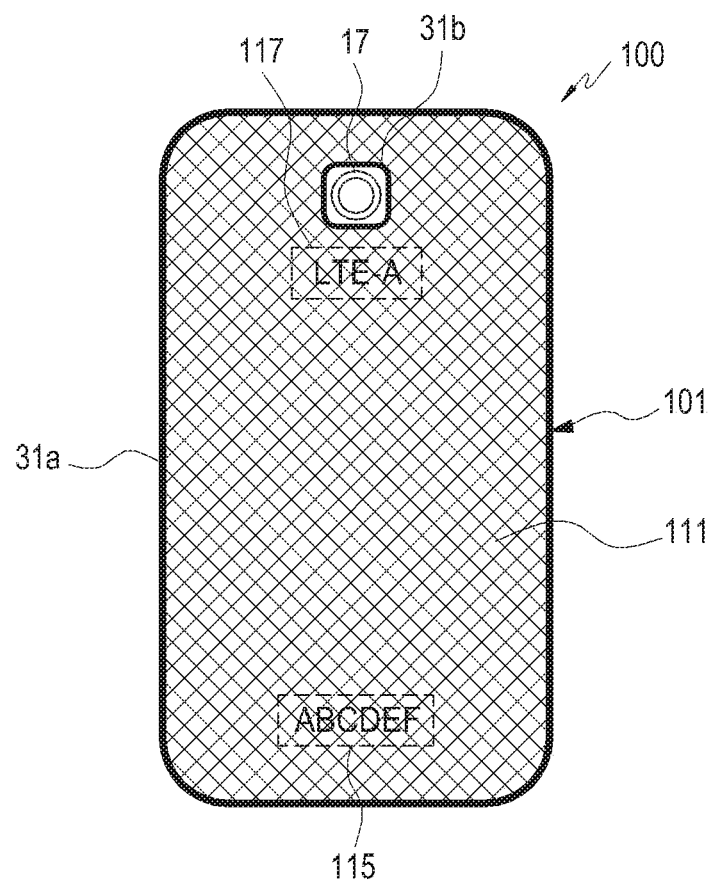
FIG. 11 is a view illustrating a portable bio information measuring device according to an embodiment of the present disclosure.
Figure 12:
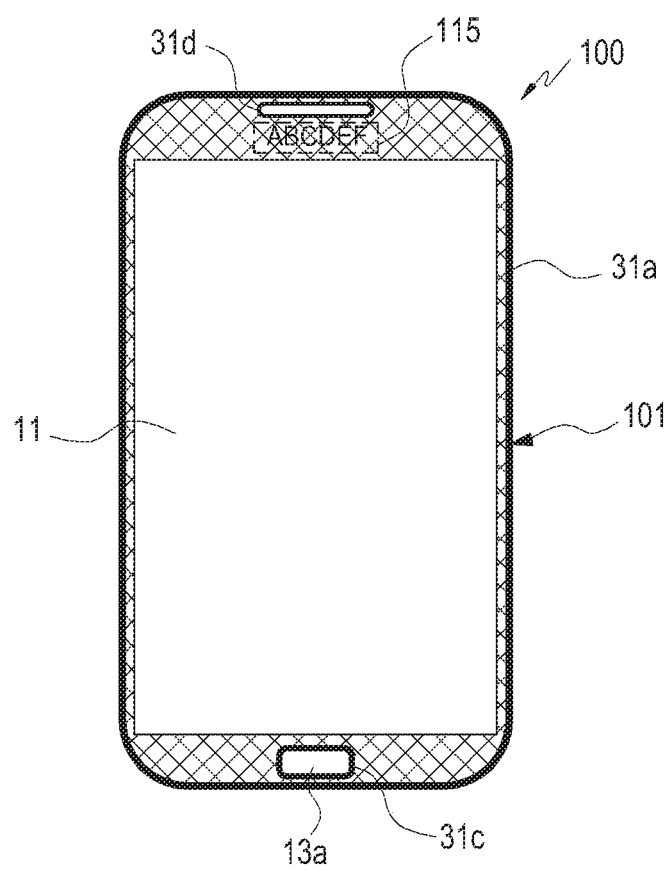
FIG. 12 is a view illustrating a portable bio information measuring device according to an embodiment of the present disclosure.

FIG. 11 is a view illustrating a portable bio information measuring device 100 according to an embodiment of the present disclosure. FIG. 12 is a view illustrating a portable bio information measuring device 100 according to an embodiment of the present disclosure.

Referring to FIGS. 11 and 12, according to an embodiment of the present disclosure, the electrodes 113 may be implemented using various decorations formed on the front or rear surface of the housing 101. Various decorations may be arranged on the outer surface of the housing 101. For example, the printed layer 117 having a drawing, e.g., the manufacturer or carrier's logo, printed on the front or rear surface of the housing 101, the surrounding edge of the housing 101, or input/output devices (e.g., the frames 31a, 31b, and 31c arranged around the camera module or button 13a), and the grill-type cover 31d disposed on the receiver unit may be formed of metal or subject to plating or deposition to allow the housing 101 an elegant appearance. According to an embodiment of the present disclosure, the printed layer 117 may be formed of a conductive ink. When the decorations, such as the printed layer 117, the frames 31a, 31b, and 31c, and the grill-type cover 31d, are formed of a conductive material, they may be used as electrodes for detecting the user's bio signals. For example, among the six letters in the printed layer 117 representing the manufacturer's logo formed on the front or rear surface of the housing 101, the left three and the right three may be configured as different electrodes, respectively. Accordingly, when one pair or more of conductive decorations 117 contact the user's body, the conductive decorations 117 may be implemented as electrodes to measure bio signal information. Thus, even when no separate electrodes 113, such as the transparent electrodes 113 or conductive printed electrodes 113, are implemented on the outer surface of the housing 101, the various conductive decorations 117 provided on the outer surface of the housing 101 may be configured as electrodes, allowing an increased degree of freedom in designing the appearance of the housing 101.

When the decorations arranged on the outer surface of the housing 101 are configured as electrodes 113 for detecting the user's bio signals, the connecting member 111 may be provided as, e.g., the via hole 111e, wire 112, or flexible circuit board 19, to be connected to the circuit device from the printed layer 117 on the outer surface of the housing 101. The connecting member 111 may be formed of any one of a conductive mesh, silver nano, or graphene, to electrically connect the printed layer 117 with the circuit board 19. Further, the connecting member 111 may be formed of the frames 31a, 31b, and 31c or grill-type cover 31d or conductive mesh to electrically connect the printed layer 117 with the circuit device.

As mentioned above, when the electrodes 113, e.g., the transparent electrodes 113, the conductive printed electrodes 113, or the conductive decoration 117, are implemented on the outer surface of the housing 101, the electrodes 113 may be implemented directly on the outer surface of the housing 101, or the electrodes 113 may be first implemented on a separate transparent film 150, and the transparent film 150 having the electrodes 113 may be seated on the outer surface of the housing 101 so that the electrodes 113 are provided on the outer surface of the housing 101. Alternatively, a base substrate 150 may be formed of glass or synthetic resin on a surface of the housing 101. The electrodes 113 may be formed on the surface of the base substrate 150. According to an embodiment of the present disclosure, the base substrate 150 may be formed of a window glass positioned on the surface of the input unit 11.

Figure 13:
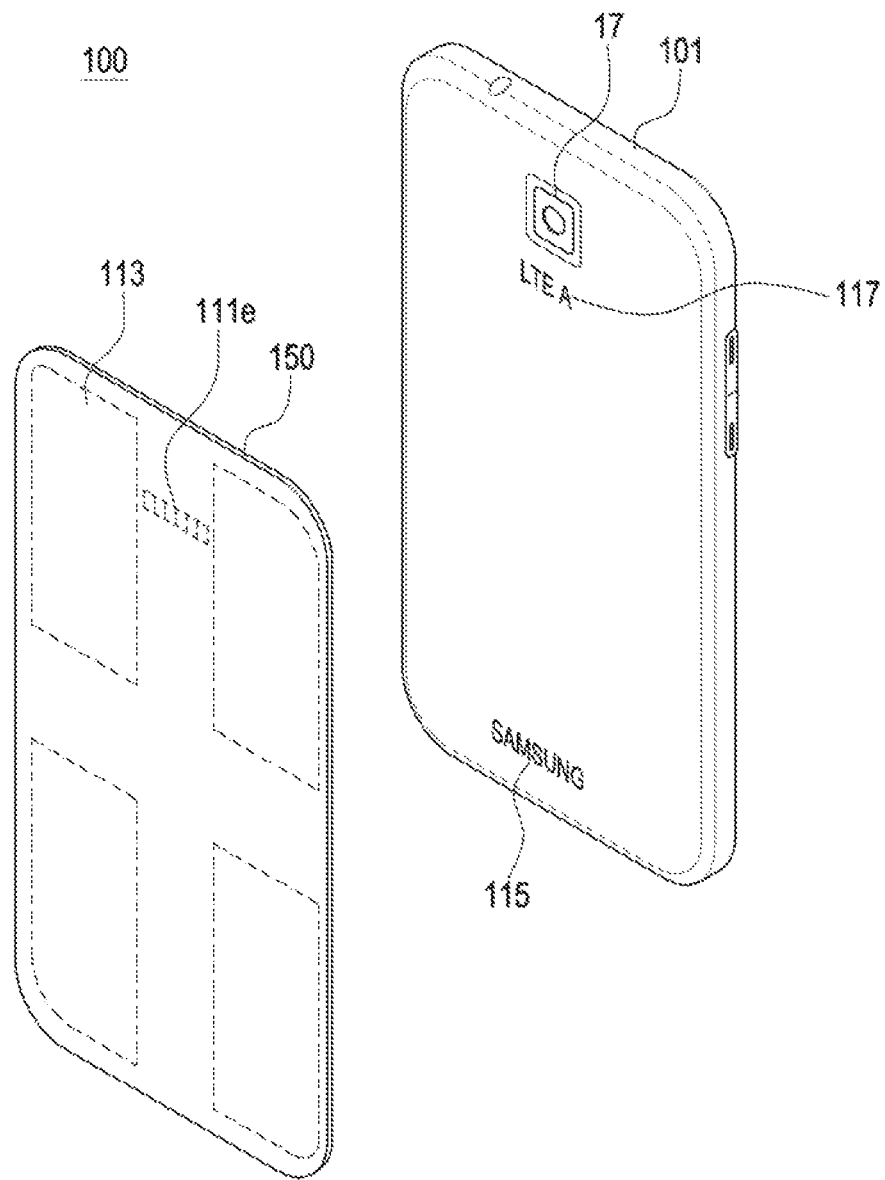
FIG. 13 is a view illustrating an example in which electrodes are formed on a transparent film or base substrate to be provided on a rear surface of a housing in a portable bio information measuring device according to an embodiment of the present disclosure.
Figure 14:
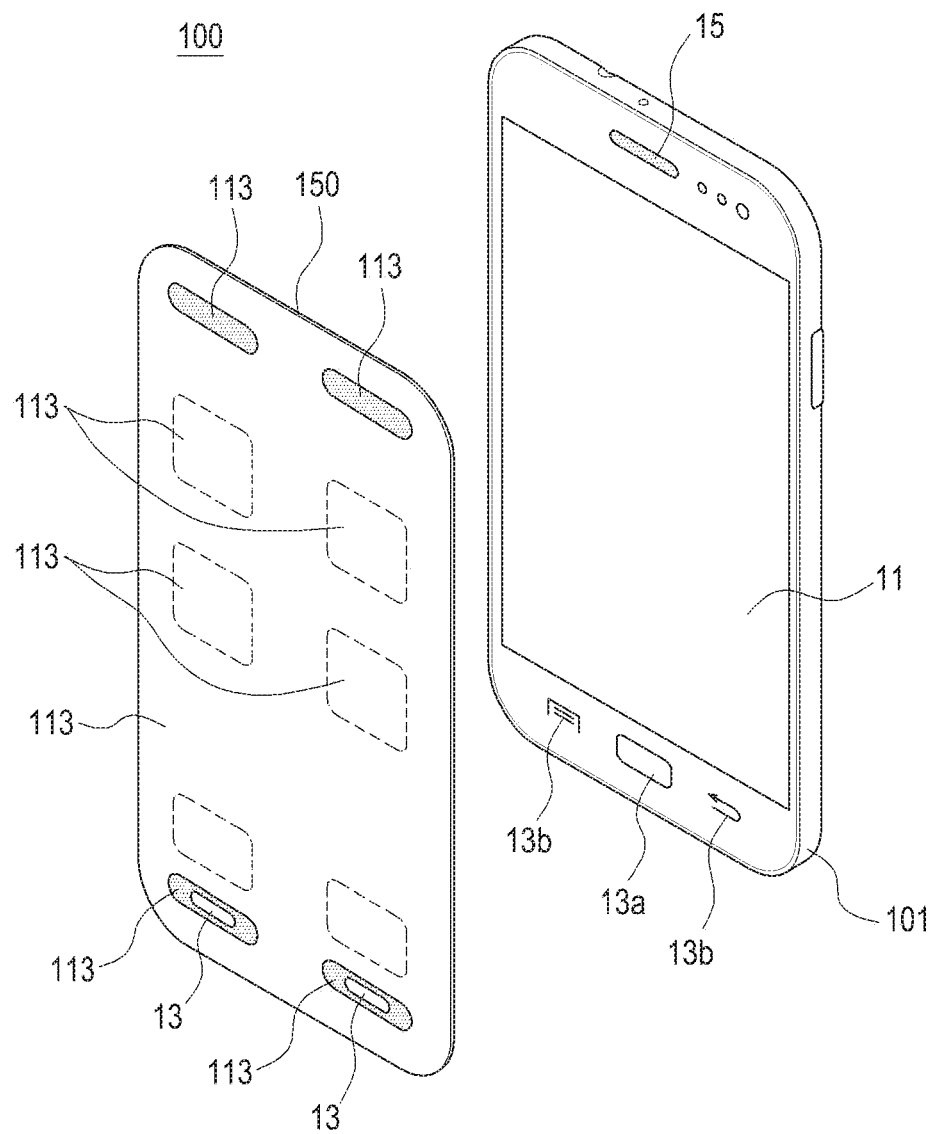
FIG. 14 is a view illustrating an example in which electrodes are formed on a transparent film or base substrate to be provided on a front surface of a housing in a portable bio information measuring device according to an embodiment of the present disclosure.

FIG. 13 is a view illustrating an example in which electrodes 113 are formed on a transparent film or base substrate 150 to be provided on a rear surface of a housing 101 in a portable bio information measuring device 100 according to an embodiment of the present disclosure. FIG. 14 is a view illustrating an example in which electrodes 113 are formed on a transparent film or base substrate 150 to be provided on a front surface of a housing 101 in a portable bio information measuring device 100 according to an embodiment of the present disclosure.

Referring to FIGS. 13 and 14, the transparent film or base substrate 150 formed of glass or synthetic resin which has electrodes 113 for detecting the user's bio signals may be placed on the rear or front surface of the housing 101. For example, the transparent film or the base substrate 150 having the electrodes 113 disposed may be provided on the rear surface of the housing 101, or alternatively, the transparent film or base substrate 150 having the electrodes 113 formed may be placed on the front surface of the housing 101 where the input unit 11 is implemented. Further, when the transparent film or base substrate 150 having the electrodes 113 are placed on the front surface of the housing 101, the electrodes 113 may be arranged to overlap the input unit 11. For example, when the touch panel is not integrated with the input unit 11, as in the instant embodiment, transparent electrodes 113 using an ITO film, e.g., the electrodes 113, may be arranged to overlap the input unit 11.

The electrodes 113 may be arranged on the rear surface of the portable bio information measuring device 100 for use in detecting the user's bio signals. The configuration of placing the electrodes 113 on the rear or front surface of the housing 101 has been described above and no further detailed description thereof is given. Further, when the electrodes 113 are placed on the outer surface of the housing 101 while mounted on the transparent film or the base substrate 150, if an antenna device(s) or other modules that may interfere with the electrodes 113 are arranged inside the housing 101, the electrodes 113 may be partially restricted in shape and array for smooth transmission/reception of the antenna device.

When the touch key 13b is disposed on the front surface of the housing 101, and some of the electrodes 113 are arranged to overlap the touch key 13b, an open area 13 for exposing the touch key 13b may be formed in the electrodes 113 overlapping the touch key 13b. The open area 13 may be implemented as an area where the conductive material (e.g., indium tin oxide) forming the electrodes 113 is not deposited. Further, the open area 13 may be implemented by forming an opening passing through the film in a portion corresponding to the touch key 13b.

Hereinafter, the connecting member 111 is described for electrically connecting the electrodes 113 to the circuit board 19 provided inside the housing 101 when the electrodes 113 (hereinafter, the electrodes 113 collectively refer to the transparent electrodes 113 or conductive printed electrodes 113) are directly implemented on an at least one outer surface of the front or rear surface of the housing 101 or positioned on the transparent film or base substrate 150.

Figure 15:
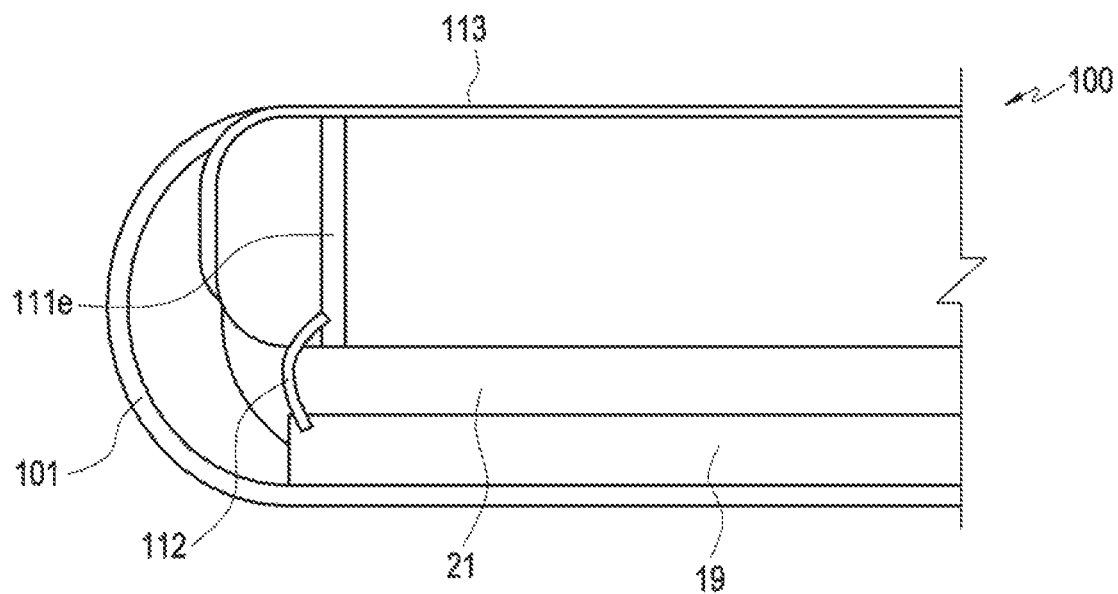
FIG. 15 is a view illustrating an embodiment of a connecting member in a portable bio information measuring device according to an embodiment of the present disclosure.

FIG. 15 is a view illustrating an embodiment of a connecting member 111 in a portable bio information measuring device 100 according to an embodiment of the present disclosure.

Referring to FIG. 15, the connecting member 111 may be provided as a via hole 111e. For example, the via hole 111e may be formed in the housing 101 to electrically connect the electrodes 113 provided on the outer surface of the housing 101 with the circuit board 19. Although not shown, the connecting member 111 may be formed of conductive plastic on a portion of the housing 101 to connect the electrodes 113 with the circuit board 19. Further, the connecting member 111 provided as the via hole 111e or a conductive portion of the housing 101 may be connected with the circuit board 19 via direct contact or a separate wire 112.

Figure 16:
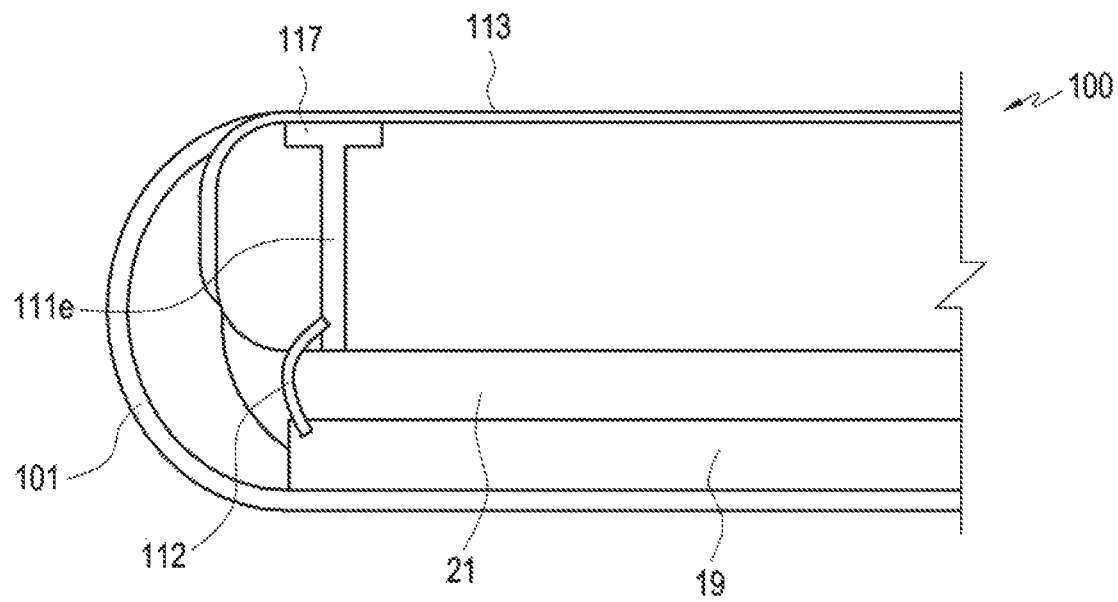
FIG. 16 is a view illustrating an embodiment of a connecting member in a portable bio information measuring device according to an embodiment of the present disclosure.

FIG. 16 is a view illustrating an embodiment of a connecting member 111 in a portable bio information measuring device 100 according to an embodiment of the present disclosure.

Referring to FIG. 16, the connecting member 111 may be implemented as various conductive decorations 117 provided on the outer surface of the housing 101. The various conductive decorations 117 may be implemented on the outer surface of the housing 101, and the conductive decorations 117 may be used to connect the electrodes 113 with the circuit board 19. For example, a trademark, logo, or a decorative drawing may be formed on the outer surface of the housing 101. Such trademark, logo, or decorative drawing may be formed of a conductive member or conductive printed layers 115 and 117 on the outer surface of the housing 101. A key, speaker device, camera device, or other modules may be arranged on the outer surface of the housing 101. The decorative frames 31a, 31b, and 31c provided around such modules may be formed of a conductive member (hereinafter, referred to as "conductive decoration"). The electrodes 113 provided on the outer surface of the housing 101 may be electrically connected with the conductive decoration 117 provided on the outer surface of the housing 101, and the conductive decoration 117 may contact the circuit board 19 directly or via a separate wire 112 or via hole 111e. Accordingly, the electrodes 113 may be electrically connected with the circuit board 19 inside the housing 101 through the conductive decoration 117.

Figure 17:
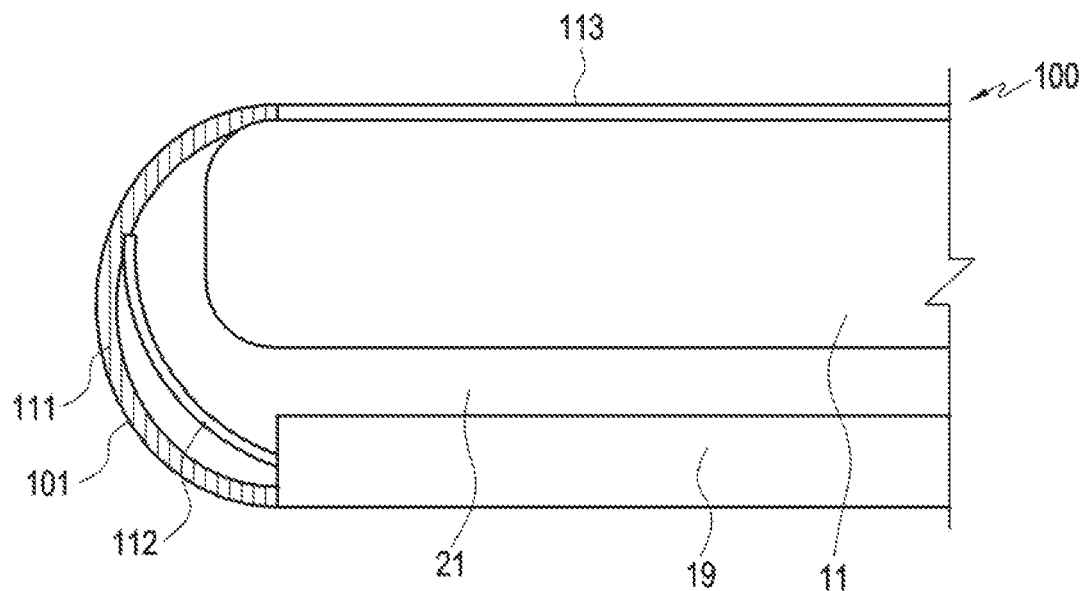
FIG. 17 is a view illustrating an embodiment of a connecting member in a portable bio information measuring device according to an embodiment of the present disclosure.

FIG. 17 is a view illustrating an embodiment of a connecting member 111 in a portable bio information measuring device 100 according to an embodiment of the present disclosure.

Referring to FIG. 17, the connecting member 111 may be provided as a conductive decoration 117 such as side frames 31a, 31b, and 31c or grill-type cover 31d arranged on the outer surface of the housing 101. For example, the side frames 31a, 31b, and 31c or the grill-type cover 31d may be implemented of a conductive member (hereinafter, referred to as conductive decoration 117). The presence of the conductive decoration 117 such as the side frames 31a, 31b, and 31c or grill-type cover 31d between the electrodes 113 and the circuit board 19 may provide an electrically connection therebetween.

The conductive decoration 117, such as the side frames 31a, 31b, and 31c or grill-type cover 31d, may contact the circuit board 19 directly or via a separate wire 112 or via hole 111e. Accordingly, the electrodes 113 may be electrically connected with the circuit board 19 inside the housing 101 through the conductive decoration 117.

Figure 18:
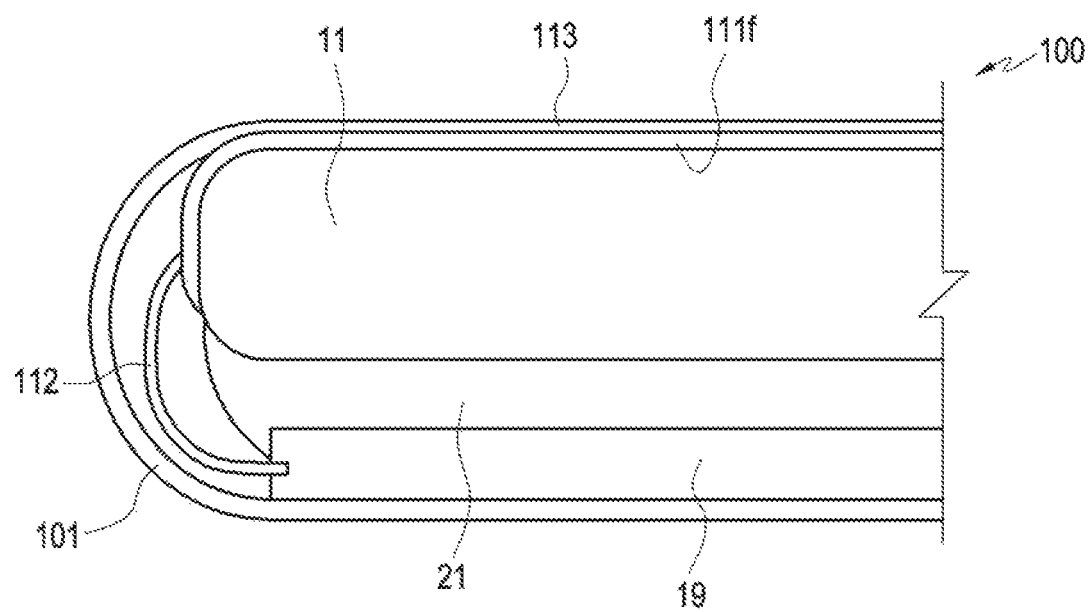
FIG. 18 is a view illustrating an embodiment of a connecting member in a portable bio information measuring device according to an embodiment of the present disclosure.

FIG. 18 is a view illustrating an embodiment of a connecting member 111 in a portable bio information measuring device 100 according to an embodiment of the present disclosure.

Referring to FIG. 18, the connecting member 111 may be formed of a wiring layer 111f on the outer surface of the housing 101. The electrodes 113, e.g., the transparent electrodes 113, the conductive printed electrodes 113, or the conductive decoration 117, may be formed on the wiring layer 111f. The wiring layer 111f may connect each of the electrodes 113 to the inside of the housing 101. The circuit board 19 and the input unit 11 supported by a bracket 21 may be arranged in the wiring layer 111f inside the electronic device 100b, and the wiring layer 111f or the electrodes 113 may be disposed on the outer surface of the housing 101. According to an embodiment of the present disclosure, the electrodes 113 and the wiring layer 111f may be formed on the outer surface of the housing 101, e.g., the rear surface of the housing 101. When the input unit 11 is provided on a surface, e.g., front surface, of the housing 101, and a touch panel is integrated with the input unit 11, the wiring layer 111f or the electrodes 113 may be arranged around the input unit 11.

The wiring layer 111f or electrodes 113 may be internally formed surrounding a portion of the input unit 11 or the housing 101. For example, when the electrodes 113 are directly formed in the housing 101, the wiring layer 111f may be formed of a circuit wire formed along the surface of the housing 101 under the electrodes 113. For example, when the lower hole 13 are provided in the transparent film 150 attached to the outer surface of the housing 101 or a base substrate 150 including a plastic portion or a glass portion, the wiring layer 111f or the electrodes 113 may be formed of circuit wires formed along the surface of the transparent film or the base substrate 150.

For example, if the electrodes 113 have the property of increasing resistance when formed with a curved surface or bend, such as indium tin oxide, the wiring layer 111f may first be formed of, e.g., a conductive mesh, on the housing 101, e.g., the surface of the housing 101, surface of the transparent film or the surface of the window glass, and the electrodes 113 may be then formed to connect with the upper portion of the wiring layer 111*f* or the wiring layer 111*f*. The wiring layer 111*f* may be connected with the circuit board 19 directly or via a separate wire 112.

Figure 19:
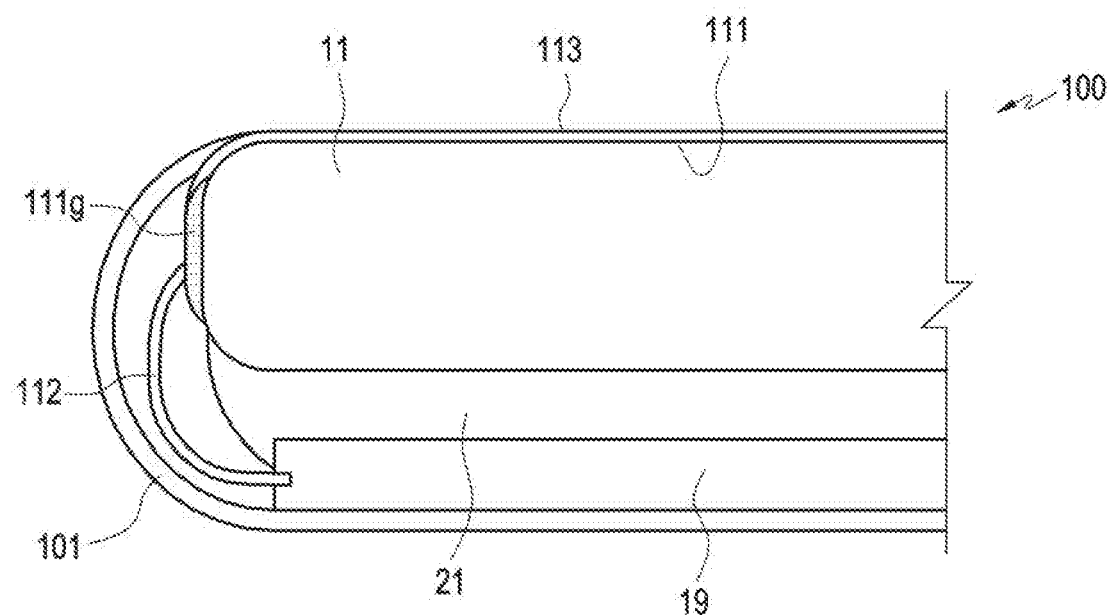
FIG. 19 is a view illustrating an embodiment of a connecting member in a portable bio information measuring device according to an embodiment of the present disclosure.

FIG. 19 is a view illustrating an embodiment of a connecting member 111 in a portable bio information measuring device 100 according to an embodiment of the present disclosure.

Referring to FIG. 19, according to an embodiment of the present disclosure, the connecting member 111 connecting the electrodes 113 with the circuit board 19 may be provided as a conductive material layer 111*g*. Specifically, the electrodes 113 of the electronic device 100 may be formed on the front surface (or rear surface) of the electronic device 100, and the conductive material layer 111*g* formed at an inside of the electronic device 100 may be formed to abut an edge of the electrodes 113. For example, the conductive material layer 111*g* may first be formed at an inside of the housing 101, and the electrodes 113 may be formed on the outer circumference of the housing 101 (e.g., the base substrate 150) to connect with the conductive material layer 111*g*. The electrodes 113 may be formed by plating or depositing a conductive material. The conductive material layer 111*g* may be formed by depositing a metal or printing with a conductive ink. The conductive material layer 111*g* inside the electronic device 100 may be connected with the circuit board 19 directly or via a separate wire 112. Accordingly, the electrodes 113 may be connected with the circuit board 19 via the conductive material layer 111*g* or the conductive material layer 111*g* and the wire 112.

Figure 20:
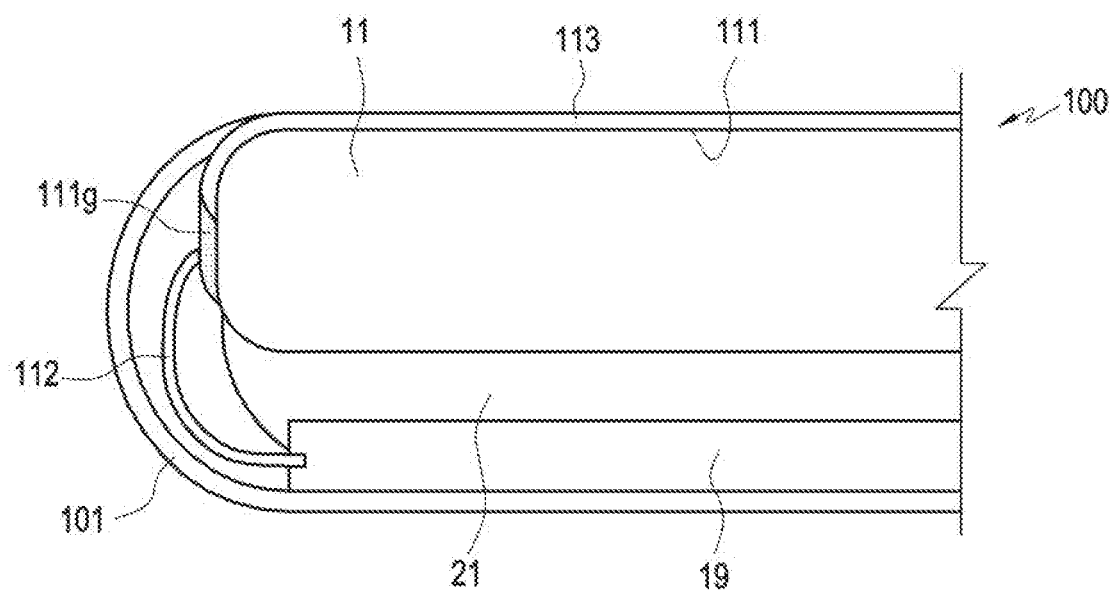
FIG. 20 is a view illustrating an embodiment of a connecting member in a portable bio information measuring device according to an embodiment of the present disclosure.

FIG. 20 is a view illustrating an embodiment of a connecting member 111 in a portable bio information measuring device 100 according to an embodiment of the present disclosure.

Referring to FIG. 20, according to an embodiment of the present disclosure, the connecting member 111 connecting the electrodes 113 with the circuit board 19 may be provided as the conductive material layer 111*g* as in the prior embodiment, but differs from the prior embodiment in light of the order of processing the conductive material layer 111*g*. According to an embodiment of the present disclosure, the electrodes 113 may be formed on the front surface (or rear surface) of the housing 101 as shown in FIG. 17, and the conductive material layer 111*g* formed inside the housing 101 may be formed to abut the edge of the electrodes 113. However, in the instant embodiment, the electrodes 113 may first be formed, and the conductive material layer 111*g* may then be formed to abut the edge of the electrodes 113 inside the housing 101. The electrodes 113 may be formed by plating or depositing a conductive material. The conductive material layer 111*g* may be formed by depositing a metal or printing with a conductive ink. The conductive material layer 111*g* inside the housing 101 may be connected with the circuit board 19 directly or via a separate wire 112. Accordingly, the electrodes 113 may be connected with the circuit board 19 via the conductive material layer 111*g* or the conductive material layer 111*g* and the wire 112.

Figure 21:
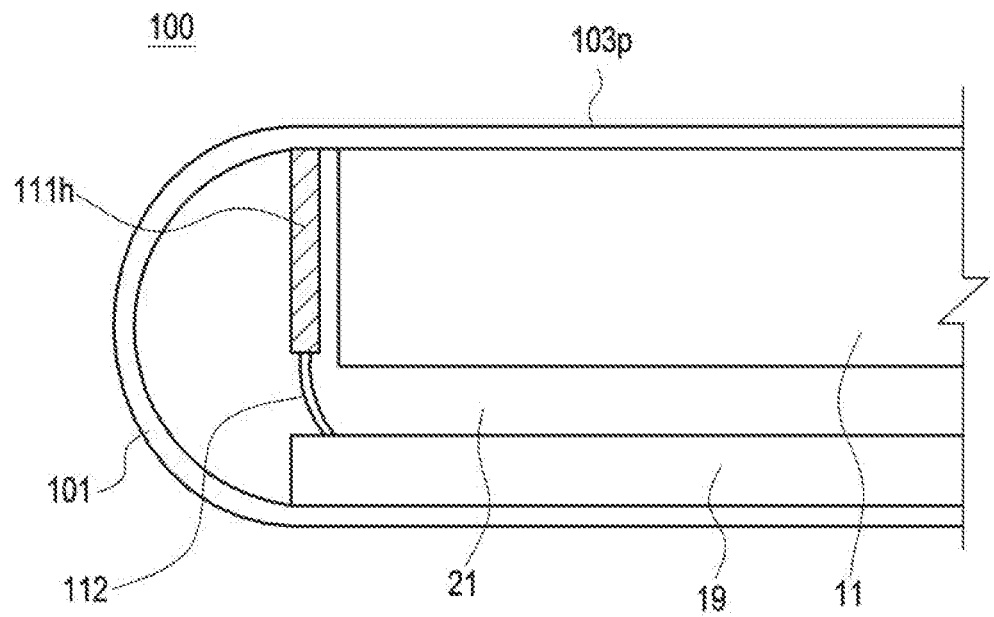
FIG. 21 is a view illustrating an embodiment of a connecting member in a portable bio information measuring device according to an embodiment of the present disclosure.

FIG. 21 is a view illustrating an embodiment of a connecting member 111 in a portable bio information measuring device 100 according to an embodiment of the present disclosure.

Referring to FIG. 21, according to an embodiment of the present disclosure, the connecting member 111 may be provided as a protruding fin 111*h* pulled in the inside of the housing 101. For example, when the electrodes 113 are arranged on the transparent film or the base substrate 150 to be provided on the outer surface of the housing 101, the protruding fin 111*h* from a surface of the transparent film or base substrate 150 to the housing 101 may pass through the housing 101 to be electrically connected directly or indirectly with the circuit board 19, e.g., via the conductive material layer 111*g* or wire 112 provided inside the housing 101. Although not shown, a slit corresponding to the protruding fin 111*h* may be formed in the housing 101, and the protruding fin 111*h* may be disposed through the slit into the inside of the housing 101 to connect with the circuit device.

Figure 22:
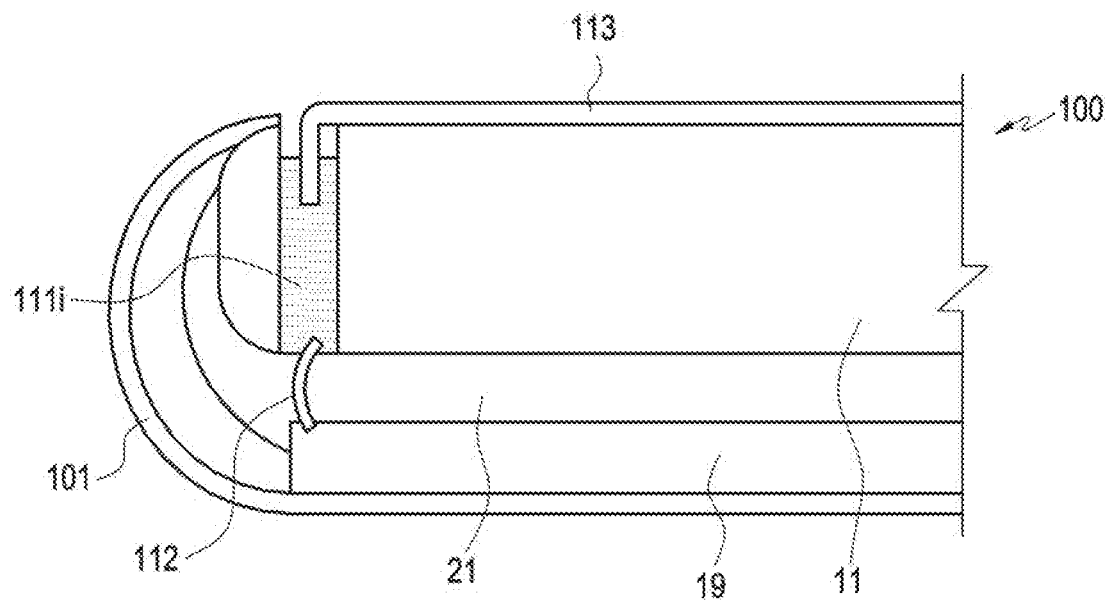
FIG. 22 is a view illustrating an embodiment of a connecting member in a portable bio information measuring device according to an embodiment of the present disclosure.

FIG. 22 is a view illustrating an embodiment of a connecting member 111 in a portable bio information measuring device 100 according to an embodiment of the present disclosure.

Referring to FIG. 22, when the transparent film or the base substrate 150 having the electrodes 113 formed is attached to the outer surface of the housing 101, a portion of the transparent film or base substrate 150 may be bent to the inside of the housing 101, allowing the electrodes 113 to connect with the circuit board 19 inside the housing 101. For example, the portion of the transparent film or the base substrate 150 disposed inside the housing 101 may have the connecting members 111 connected with the electrodes 113. The connecting members 111 may be formed of transparent electrodes 113, e.g., a conductive mesh, silver nano, or graphene. The portion of the transparent film or the base substrate 150 inside the housing 101 may be connected with the wire 112 through the conductive material layer 111*g*, and the wire 112 may connect the portion of the transparent film 150 with the circuit board 19.

As described below, the connecting structure having the shape shown in FIG. 22 may be utilized in the cover structure detachably coupled to the portable bio information measuring device 100. For example, a connecting member or protruding fin 111*i* may be formed on an inner surface of the cover unit 200 similarly to the bend of the transparent film 150, and its corresponding slit may be formed in the body of the portable bio information measuring device 100. When the protecting cover is coupled with the body, the protruding fin 111*i* may be placed through the slit into the inside of the body to couple with the circuit board 19.

Figure 23:
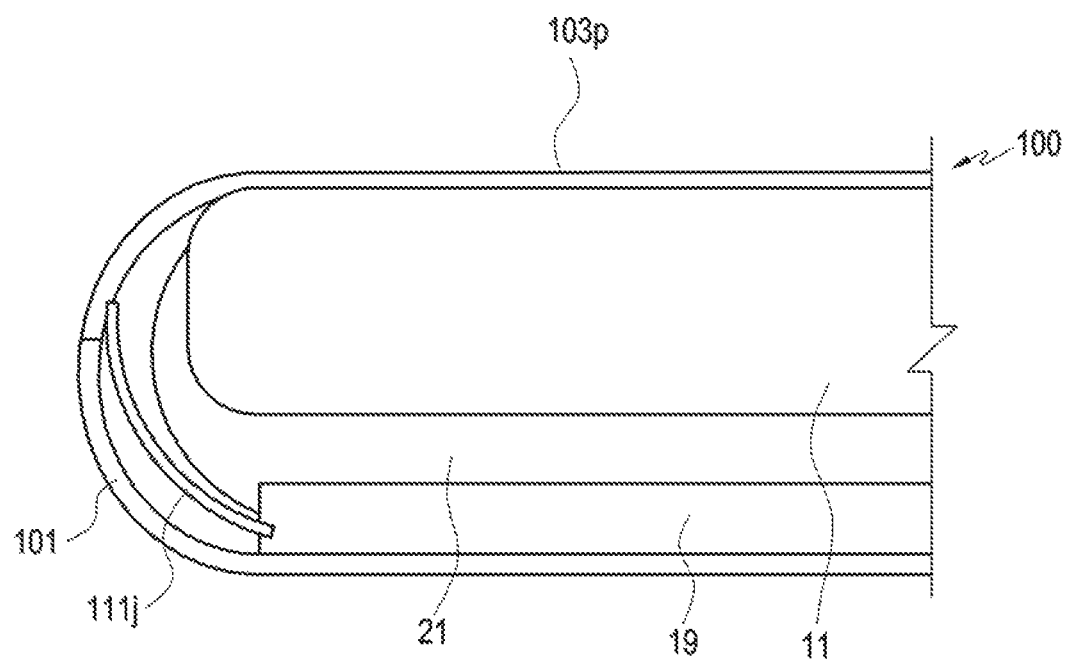
FIG. 23 is a view illustrating an embodiment of a connecting member in a portable bio information measuring device according to an embodiment of the present disclosure.

FIG. 23 is a view illustrating an embodiment of a connecting member 111 in a portable bio information measuring device 100 according to an embodiment of the present disclosure.

Referring to FIG. 23, a connecting member or connecting pin 111*j* may be exposed which is connected with the circuit board 19 on the outer surface of the housing 101. For example, the connecting pin 111*j* may be formed of a contacting terminal, such as a plate spring, C-clip, or pogo pin. When the transparent film or the base substrate 150 is attached to the housing 101, the connecting pin 111*j* may contact the connecting members 111 (or electrodes 113) formed on the transparent film or the base substrate 150 to connect the electrodes 113 with the circuit board 19.

Figure 24:
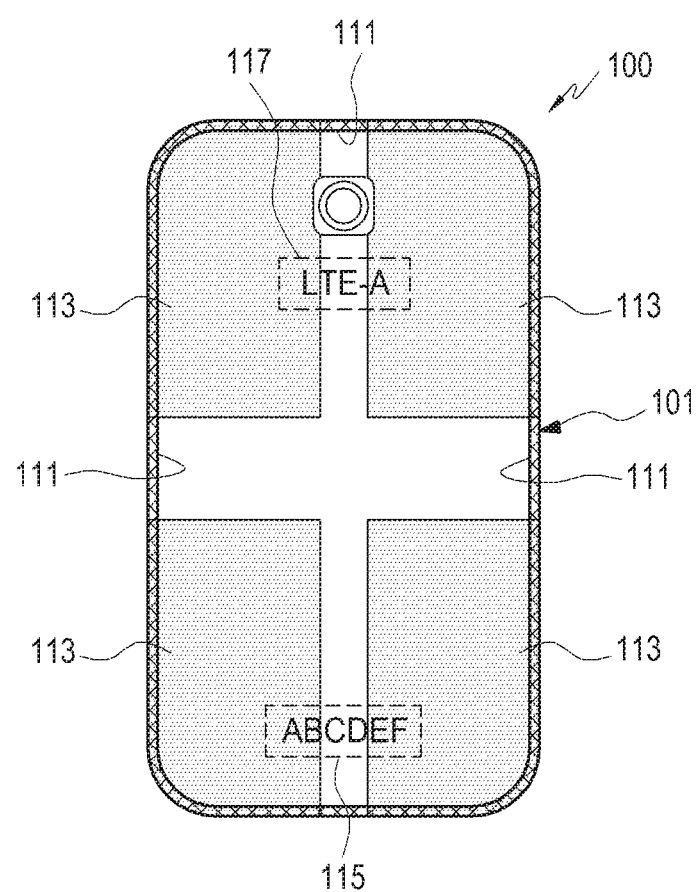
FIG. 24 is a view illustrating a rear surface of a housing having a connecting member overlapping electrodes in a portable bio information measuring device according to an embodiment of the present disclosure.
Figure 25:
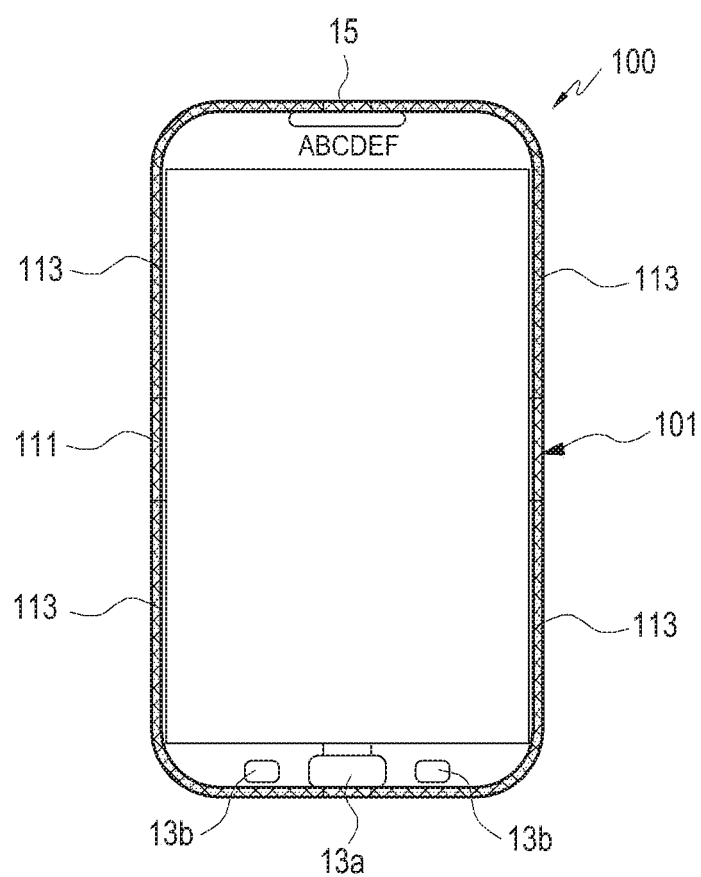
FIG. 25 is a view illustrating a front surface of a housing having a connecting member overlapping electrodes in a portable bio information measuring device according to an embodiment of the present disclosure.
Figure 26:
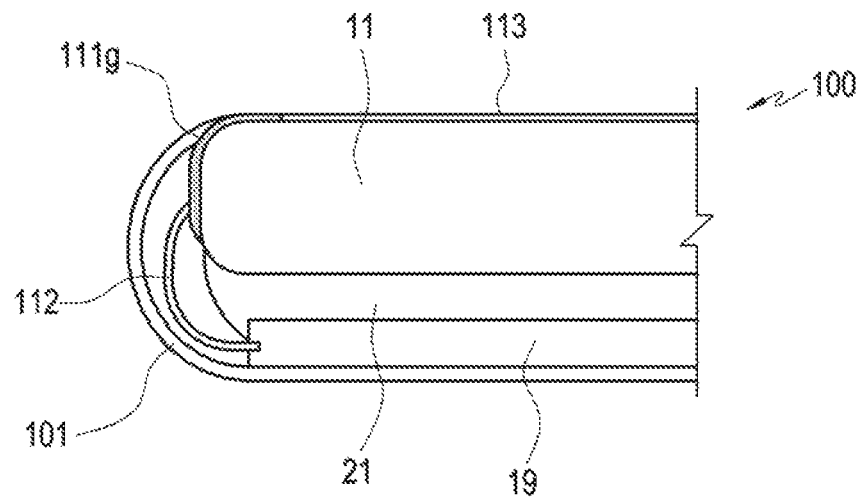
FIG. 26 is a cross-sectional view illustrating a housing having a connecting member overlapping electrodes in a portable bio information measuring device according to an embodiment of the present disclosure.

FIG. 24 is a view illustrating a rear surface of a housing having a connecting member 111 overlapping electrodes 113 in a portable bio information measuring device 100 according to an embodiment of the present disclosure. FIG. 25 is a view illustrating a front surface of a housing having a connecting member 111 overlapping electrodes 113 in a portable bio information measuring device 100 according to an embodiment of the present disclosure. FIG. 26 is a cross-sectional view illustrating a housing having a connecting member 111 overlapping electrodes 113 in a portable bio information measuring device 100 according to an embodiment of the present disclosure, which is an embodiment of the connecting member.

Referring to FIGS. 24 to 26, according to an embodiment of the present disclosure, the portable bio information measuring device 100 may include connecting members 111 formed on the outer surface of the housing 101 and electrodes 113 at least partially overlapping the connecting members 111. The electrodes 113 may be formed around the input unit 11 on the front surface of the housing 101 to completely overlap some of the connecting members 111. The electrodes 113 may be formed of transparent electrodes 113 (e.g., indium tin oxide) deposited on the outer surface of the housing 101. At least some of the electrodes 113 may overlap the connecting members 111. The connecting members 111 may be formed of a transparent material, such as a conductive mesh, silver nano, or graphene, and since the plurality of electrodes 113 are formed on the rear or front surface of the housing 101, various bio signals may be detected according to combinations of the electrodes 113 contacting the user's body.

Further, the connecting members 111 may be formed along the edge of the rear or front surface of the housing 101. For example, the connecting members 111 may overlap a portion of the surrounding edge of the electrodes 113 provided on the outer surface of the housing 101. The connecting members 111 may be connected with the circuit board 19 directly or via a separate wire 112 or flexible circuit board 19 inside the housing 101. According to an embodiment of the present disclosure, the connecting members 111 may be replaced with the conductive material layer 111g described in connection with the prior embodiments.

According to the above embodiments, the connecting member 111 may be provided as, e.g., a conductive mesh, silver nano, graphene, or various conductive connecting parts, e.g., a flexible circuit board 19. For example, an end of the conductive mesh, silver nano graphene, or flexible circuit board 19 may be provided to be connected with an end of the electrodes 113 formed on the outer surface of the housing 101, to be connected with the electrodes 113 via an end of the transparent film 150, or the to be connected with the electrodes 113 via an end of the base substrate 150. The other end of the conductive mesh, silver nano graphene, or flexible circuit board 19 may be provided to be connected with the inside of the housing 101.

When the electrodes 113 are provided on the transparent film 150, the outer circumference of the transparent film 150 may be bent to the inside of the housing 101, and the connecting member 111 provided or connected with an end of the transparent film 150 may be electrically connected with the circuit board 19 directly or via a separate wire 112 or conductive material layer 111g.

FIGS. 27 to 32 disclose applications of the portable bio information measuring device 100 according to embodiments of the present disclosure.

Figure 27:
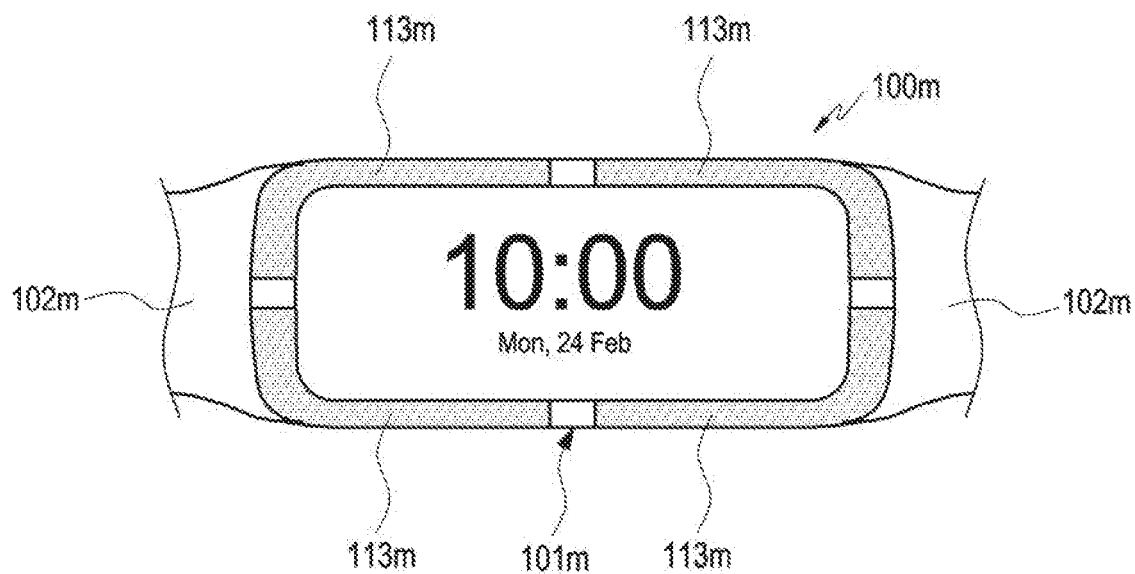
FIG. 27 is a view illustrating an example in which a portable bio information measuring device is implemented as a wearable portable bio information measuring device according to an embodiment of the present disclosure.
Figure 28:
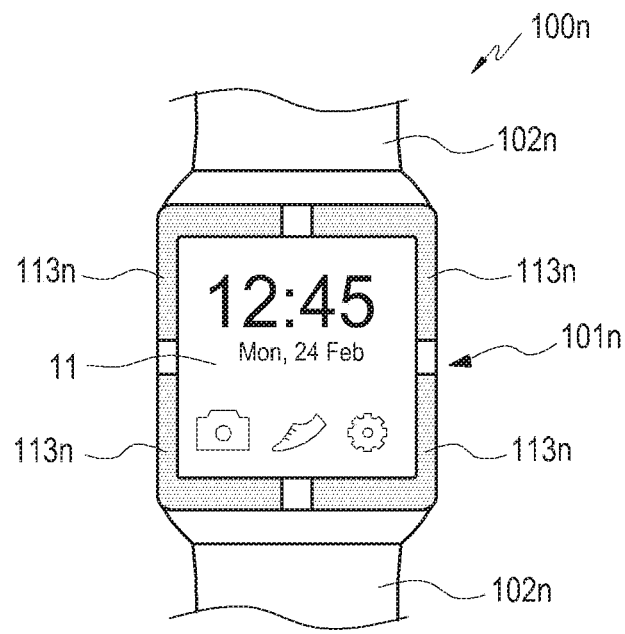
FIG. 28 is a view illustrating another example in which a portable bio information measuring device is implemented as a wearable portable bio information measuring device according to an embodiment of the present disclosure.

FIG. 27 is a view illustrating an example in which a portable bio information measuring device 100 is implemented as a wearable portable bio information measuring device 100m according to an embodiment of the present disclosure. FIG. 28 is a view illustrating another example in which a portable bio information measuring device 100 is implemented as a wearable portable bio information measuring device 100n according to an embodiment of the present disclosure.

Referring to FIGS. 27 and 28, according to an embodiment of the present disclosure, the portable bio information measuring device 100 may be implemented as wearable (e.g., wrist-worn) portable bio information measuring devices 100m and 100n. The portable bio information measuring devices 100m and 100n may include bodies 101m and 101n and wearing portions 102m and 102n respectively extending from the bodies 101m and 101n. The user may wear the portable bio information measuring devices 100m and 100n on his body portion, e.g., a wrist, using the wearing portions 102m and 102n.

The bodies 101m and 101n may include an input unit 11 installed on the front surface thereof, and a plurality of electrodes 113m and 113n may be arranged around the input unit 11. When the user's body contacts some of the electrodes 113m and 113n, the portable bio information measuring devices 100m and 100n may detect the user's bio information. The electrodes 113m and 113n may be formed of conductive printed layers 115 and 117 or transparent electrodes 113 as described above, and the bodies 101m and 101n may include connecting members 111 connecting the electrodes 113m and 113n with the internal circuit device.

Although not shown, like in the above-described embodiments, a plurality of electrodes 113 may be arranged on the rear surface of the bodies 101m and 101n. While the user wears the portable bio information measuring devices 100m and 100n, the rear surfaces of the bodies 101m and 101n may remain contacting the user's skin. For example, such hassle may be removed that the user himself contacts the electrodes arranged in the body 101m or 101n while wearing the portable bio information measuring device 100m or 100n. In another embodiment, different bio signals may be detected according to combinations of the electrodes 113 contacted by the user's body, and as necessary, the user may bring another body portion in contact with at least one of the electrodes 113m and 113n arranged on the front surface of the body 100m or 101n even while wearing the portable bio information measuring device 100m or 100n.

Figure 29:
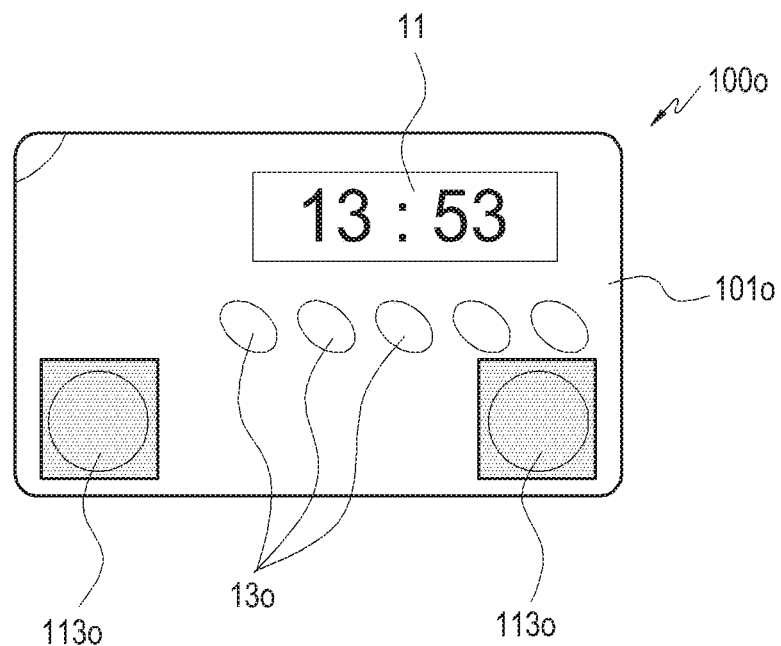
FIG. 29 is a view illustrating an example in which a portable bio information measuring device is implemented as a card-type portable bio information measuring device according to an embodiment of the present disclosure.

FIG. 29 is a view illustrating an example in which a portable bio information measuring device 100 is implemented as a card-type portable bio information measuring device 100o according to an embodiment of the present disclosure.

Referring to FIG. 29, the portable bio information measuring device 100o may be shaped as a name card or credit card, with an input unit 11 installed on a surface thereof. At least one button 13a (or touch key 13o) may be disposed on a side of the input unit 11 to receive the user's manipulation for switching modes of the portable bio information measuring device 100o, running various applications, or outputting stored information. Electrodes 113o, arranged in the body 101o, for detecting the user's bio signals may be arranged on a surface of the portable bio information measuring device 100o. The electrodes 113o may be connected with the internal circuit device via the connecting members 111, and the connecting members 111 connecting the electrodes 113o with the circuit device may be implemented by forming, e.g., a decorative design formed on a surface of the portable bio information measuring device 100o with a conductive mesh, silver nano, or graphene. When the buttons 13o are configured to operate by a mechanical contact, the electrodes 113o may be arranged to overlap the buttons 13o.

Figure 30:
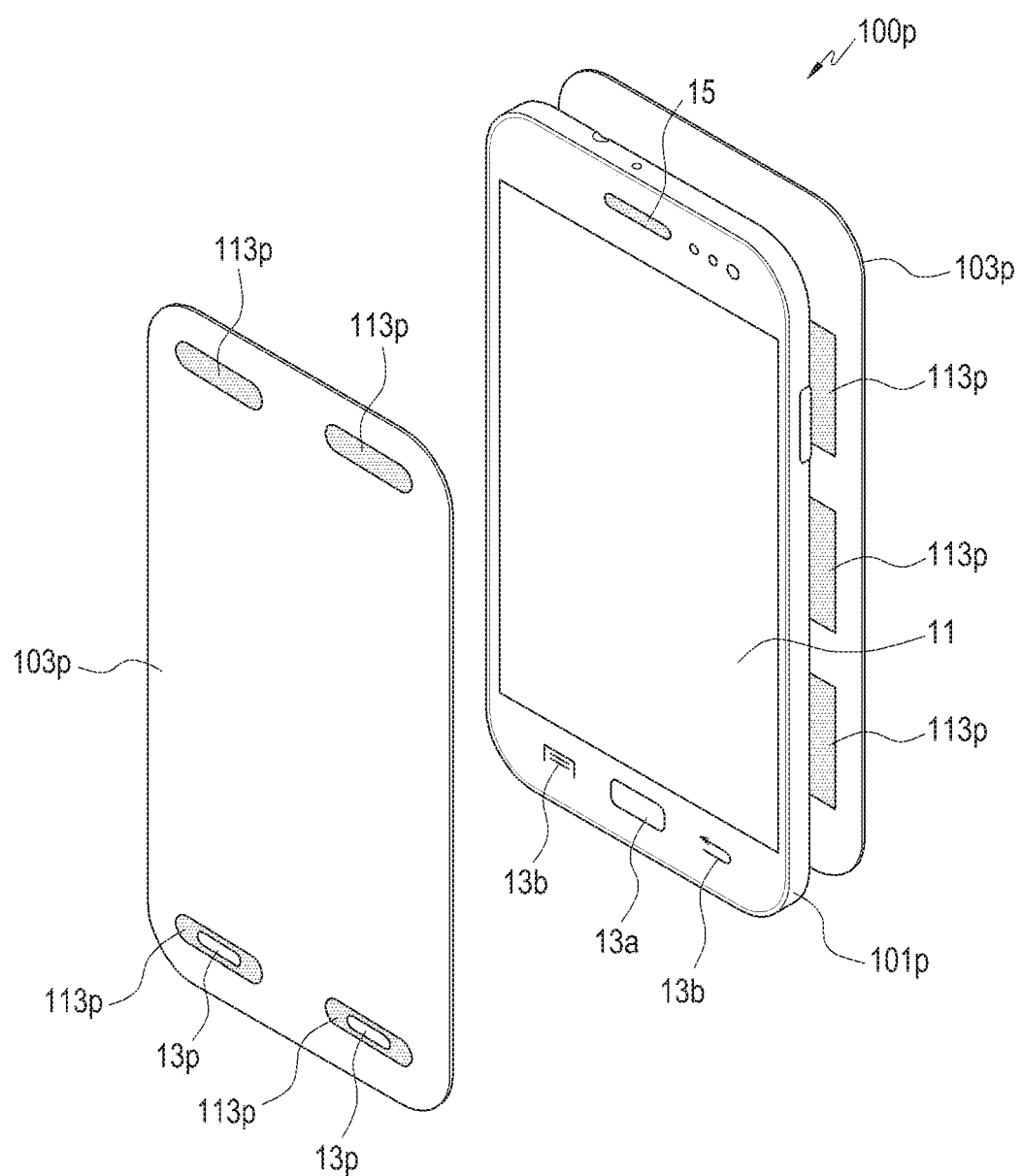
FIG. 30 is a view illustrating an example in which a portable bio information measuring device is implemented as a bar-shaped electronic device according to an embodiment of the present disclosure.

FIG. 30 is a view illustrating an example in which a portable bio information measuring device 100 is implemented as a bar-shaped electronic device according to an embodiment of the present disclosure.

Referring to FIG. 30, the portable bio information measuring device 100p may include a film 103p (e.g., a protecting film) attached to the outer surface of the housing 101p, and electrodes 113p for detecting the user's bio signals may be formed on the film 103p. On the front surface of the portable bio information measuring device 100p, the electrodes 113p may be arranged around the input unit 11 not to overlap the input unit 11. For example, when a touch panel is integrated with the input unit 11, the electrodes 113p may be arranged around the input unit 11 to prevent the recognition capability of the touch panel from being distorted. The electrodes 113p may be arranged relatively freely on the rear surface of the portable bio information measuring device 100p. However, when antenna device(s) are arranged inside the portable bio information measuring device 100p, the shape and array of the electrodes 113p may be partially restricted to provide smooth communication of the antenna device.

When the touch key 13b is disposed on the front surface of the portable bio information measuring device 10p, and some of the electrodes 113p are arranged to overlap the touch key 13b, an open area 13b may be formed in some of the electrodes 113p to expose the touch key 13b. The open area 13p may be implemented as an area where the conductive material (e.g., indium tin oxide) forming the electrodes 113p is not deposited. Further, the open area 13p may be implemented by forming an opening passing through the film 103p in a portion corresponding to the touch key 13b.

Figure 31:
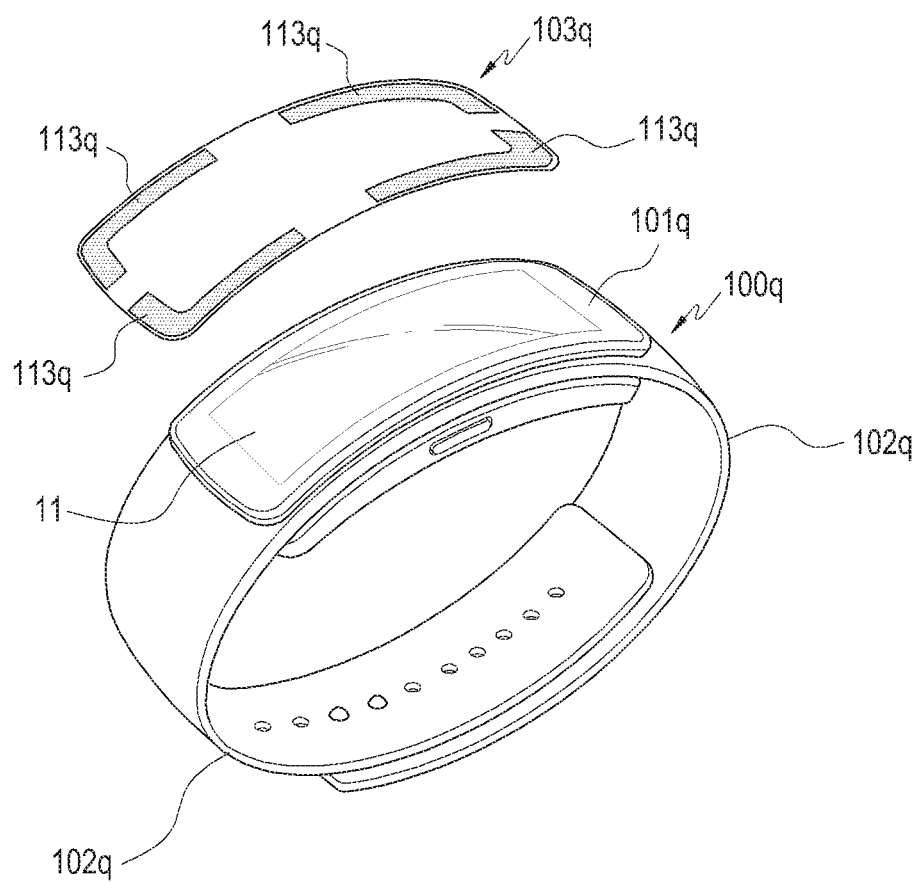
FIG. 31 is a view illustrating an example in which a portable bio information measuring device is implemented as a wearable portable bio information measuring device according to an embodiment of the present disclosure.

FIG. 31 is a view illustrating an example in which a portable bio information measuring device 100 is implemented as a wearable portable bio information measuring device 100 according to an embodiment of the present disclosure.

Referring to FIG. 31, the portable bio information measuring device 100q may include a body 101q and wearing members 102q each extending from the body 101q. In the position worn on the user's body, the wearing members 102q may have their ends coupled together to allow the portable bio information measuring device 100q to remain a closed loop, so that the user may wear the portable bio information measuring device 100q in a stable position. The body 101q may include an input unit 11. As self-explanatory, the wearable portable bio information measuring device 100 may have a narrow space for installing various input/output devices provided in the body 101q. Accordingly, a touch panel may be integrated with the input unit 11, so that the input unit 11 may be utilized as an input device.

A film (e.g., a protecting film) 103q having electrodes 113q formed may be attached to the outer surface (e.g., the front or rear surface) of the portable bio information measuring device 100q. The electrodes 113q may be formed by depositing an indium tin oxide, and may be implemented to be transparent in a real-life product. The electrodes 113q may be arranged around the input unit 11 to prevent a distortion of the recognition capability of the touch panel integrated with the input unit 11. Although no touch panel is integrated with the input unit 11 or the electrodes 113q are arranged to overlap, as long as there is no influence on the recognition capability of the touch panel, the electrodes 113q may have further diversified shapes or arrays.

Figure 32:
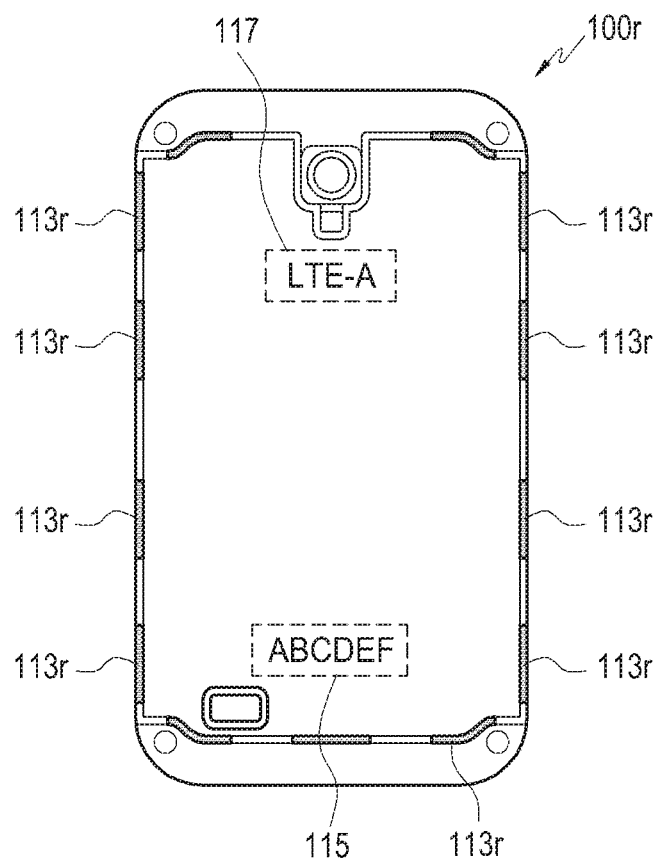
FIG. 32 is a view illustrating an example in which a portable bio information measuring device is implemented as a bar-shaped portable bio information measuring device according to an embodiment of the present disclosure.

FIG. 32 is a view illustrating an example in which a portable bio information measuring device 100 is implemented as a bar-type portable bio information measuring device 100 according to an embodiment of the present disclosure.

Referring to FIG. 32, electrodes 113r arranged on the rear surface of the portable bio information measuring device 100r may be arranged along an edge on the rear surface of the portable bio information measuring device 100r. The electrodes 113r may be implemented as a printed layer 117 or deposited layer formed by printing or depositing on a separate film, and the film having the electrodes 113r formed may be attached to the rear surface of the portable bio information measuring device 100r. When the antenna device is disposed inside the portable bio information measuring device 100r or in a predetermined area of the rear surface, the electrodes 113r may be arrayed along an edge on the rear surface of the portable bio information measuring device 100r, preventing a performance deterioration of the antenna device due to the electrodes 113r. For example, the portable bio information measuring device 100 may have multiple antenna devices arranged therein, such as an antenna for accessing a commercial communication network, an antenna for near field communication (NFC), aLAN access, or antenna for wireless charging. When such antenna devices overlap the electrodes 113r, the antenna devices may exhibit a deteriorated capability. However, according to an embodiment of the present disclosure, the portable bio information measuring device 100 may arrange the electrodes 113 for detecting the user's bio signals to prevent the antenna devices from deteriorating in capability.

A structure is now described with reference to FIGS. 33 to 39, in which the electrodes 113 for measuring the user's bio information are implemented in a cover device, and the cover device is coupled with an electronic device, e.g., the housing 101, to connect with the electronic device.

Figure 33:
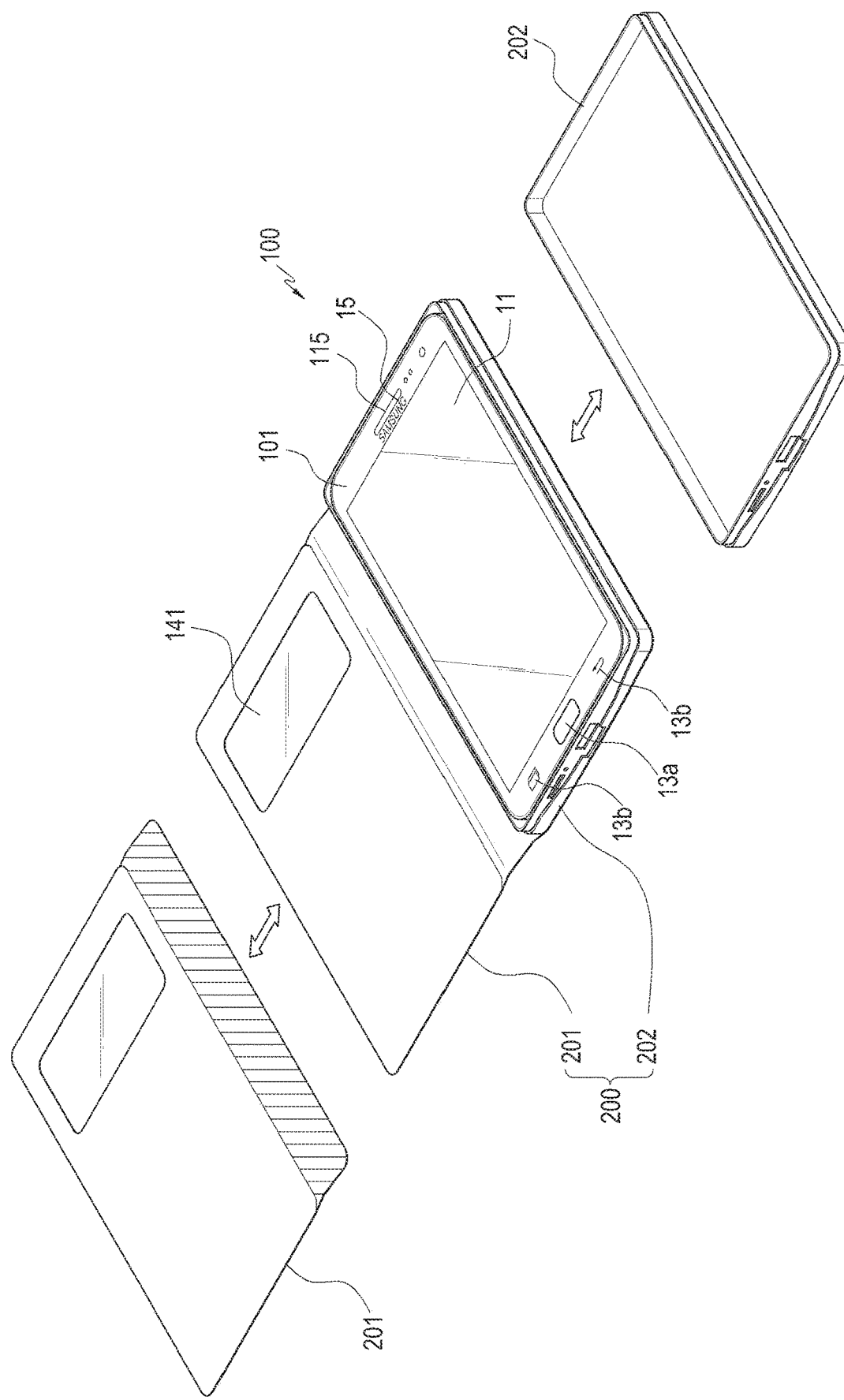
FIG. 33 is a schematic view illustrating an example in which a portable bio information measuring device is provided in a cover unit according to an embodiment of the present disclosure.

FIG. 33 is a schematic view illustrating an example in which a portable bio information measuring device 100 is provided in a cover unit 200 according to an embodiment of the present disclosure.

Referring to FIG. 33, according to an embodiment of the present disclosure, the portable bio information measuring device 100 may include a circuit board 19, a housing 101, a cover unit 200, electrodes 113, and the connecting member 111.

The circuit board 19 is a structure received in the housing 101. Various integrated circuit chips such as an application processor, memory, or communication module may be mounted on the circuit board 19. Further, the electrodes 113 provided in the cover unit 200 for detecting bio signals described below may be electrically connected with the circuit board 19 in various manner (refer to FIGS. 15 to 26).

Various components, such as a bracket 21 (refer to FIGS. 15 to 26 as well) or circuit board 19 (refer to FIGS. 15 to 26 as well) may be placed inside the housing 101. Further, at least a surface of the housing 101, specifically a front surface of the housing 101, may have a device capable of displaying screen or implementing an input, e.g., an input unit 11 including a display unit (not shown) such as a LCD or touch panel (not shown), a keypad or a receiving part. Another surface of the housing 101, specifically a rear surface of the housing 101, may include a camera module or fingerprint recognition device or other modules installed thereon. The keypad may include a button 13a operated by mechanical manipulation and a touch key 13b operated by the user's body contact. Although mentioned above, the input unit 11 may be equipped with a touch panel to output screen, and the input unit 11 may also be used as an input device.

As mentioned above, the input unit 11 may be provided in at least one surface of the housing 101 to implement a touch input. According to an embodiment of the present disclosure, the input unit 11 may be, e.g., a large-size display apparatus including a touch panel and a display unit. Thus, the input unit 11 may be utilized as an input device as well as outputs screen. However, the configuration of the input unit 11 is not limited thereto.

According to an embodiment of the present disclosure, one or more pairs of electrodes 113 may be provided in the cover unit 200 to detect the user's bio signals. The electrodes 113 may have various structures, shapes or configurations. For example, the electrodes 113 according to the present disclosure may be arranged as transparent electrodes 113 on an outer surface of the cover unit 200, otherwise as conductive printed electrodes 113 on the outer surface of the cover unit 200, or otherwise arranged using a conductive decoration 117 provided in the cover unit 200.

When the electrodes 113 are provided as transparent electrodes 113, they may be arranged without influencing the look or design of the cover unit 200. By contrast, when the electrodes 113 are provided as conductive printed electrodes 113, a design, such as a regular or irregular pattern, may be formed on the outer surface of the housing 101. Further, when the electrodes 113 are provided as a conductive decoration 117, various logos, patterns, letters, or shapes may be mounted or arranged on the outer surface of the cover unit 200 and may be simultaneously utilized as electrodes 113 that are able to measure bio information.

Further, the electrodes 113 may be directly formed on the outer surface of the cover unit 200 or may be implemented so that they are formed on the transparent film or the base substrate 150 formed of glass or synthetic resin and coupled with the cover unit 200. Further, the electrodes 113 may be formed by depositing or plating a conductive material on the outer surface of the cover unit 200 or a transparent film or base substrate 150 that may be provided on the outer surface of the cover unit 150.

The connecting member 111 is a component that electrically connects the electrodes 113 to the housing 101, specifically, the circuit board 19 implemented inside the housing 101. The connecting member 111 may have various embodiments depending on the structure of the cover unit 200. For example, the connecting member 111 may be formed as the via hole 111e between the electrode 113 and the circuit board 19, may be formed of conductive decoration 117 implemented on the outer surface of the housing 101 and electrically connected with the circuit board 19 via the conductive decoration 117, may be formed of decorative metal frames 31a, 31b, and 31c surrounding various modules provided in the housing 101 to be electrically connected with the circuit board 19 via the metal frames 31a, 31b, and 31c of the modules, or may be formed of frames 31a, 31b, and 31c provided on the side of the edge of the housing 101 to be electrically connected with the circuit board 19 via the side frames 31a, 31b, and 31c of the housing 101. Further, the connecting member 111 may be implemented as at least one of a conductive ink, a flexible printed circuit board, and a conductive mesh and may be formed of the same or different material from the electrodes 113. What has been described above for the material of the connecting member 111 may apply here.

According to an embodiment of the present disclosure, the cover unit 200 may have three structures, as at least one of e.g., a first cover member 201 (refer to FIGS. 33 and 34) covering a surface (front surface) of the housing 101 having the input unit 11, a second cover member 202 (refer to FIGS. 33 and 35) covering another surface (rear surface) positioned opposite the surface of the housing 101 having the input unit 11, or a third cover member 200 having a first cover part 201 covering a surface of the housing 101 having the input unit 11 and a second cover part 202 coupled with the first cover part 201 and covering the other surface, which is an opposite surface of the housing 101 (refer to FIG. 33).

The electrodes 113 may be directly provided on the outer surface of the first cover member 201 or the second cover member 202, or the electrodes 113 may be arranged on the transparent film 150 provided on the outer surface of the first cover member 201, the second cover member 202, or the third cover member 200 or the base substrate 150 formed of glass or synthetic resin on the outer surface of the first cover member 201, second cover member 202, or the third cover member 200 to be provided on the outer surface of the housing 101.

The electrodes 113 provided on the outer surface of the cover unit 200 may be the same in material, shape or structure as the electrodes 113 provided in the housing 101 described above, but differ in the position of installation, e.g., they may be provided in the housing 101 or the cover unit 200. Accordingly, the electrodes 113 remain the same except for the position of installation, and the above description of the electrodes 113 may apply here.

Figure 34:
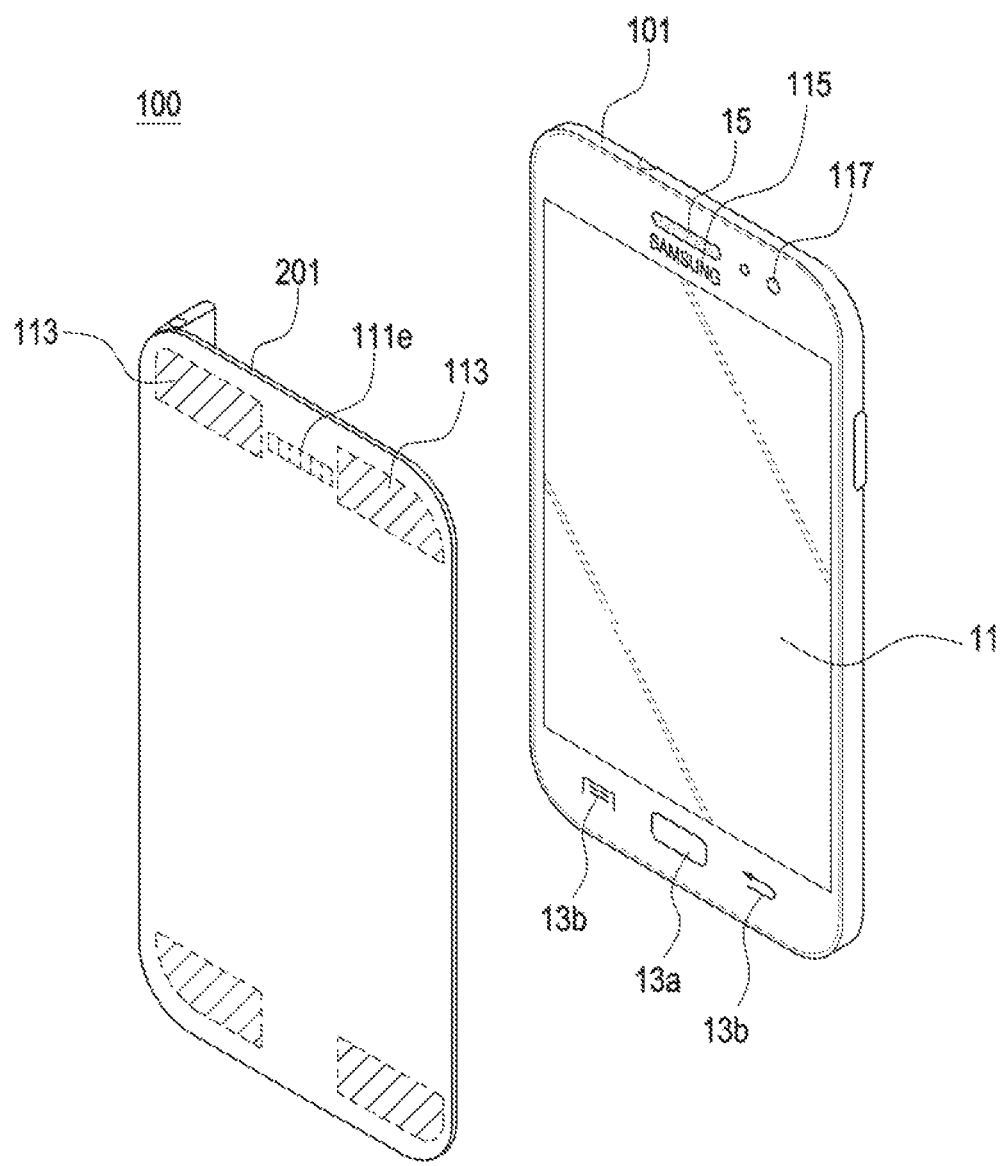
FIG. 34 is a view illustrating an embodiment of a cover unit having electrodes and a connecting member in a portable bio information measuring device according to an embodiment of the present disclosure.

FIG. 34 is a view illustrating an embodiment of a cover unit 200 including electrodes 113 and a connecting member 111 in a portable bio information measuring device 100 according to an embodiment of the present disclosure.

Referring to FIG. 34, the electrodes 113 may be provided on the outer surface of the first cover member 201, and the electrodes 113 may be arranged in an entire surface of the first cover member 201 or at, at least one, of positions corresponding to a surrounding edge of the input unit 11.

When the electrodes 113 are arranged in the entire surface of the first cover member 201 or at, at least, one of the positions corresponding to the surrounding edge of the input unit 11, the connecting member 111 may be provided as the via hole 111e, or alternately, may be provided as the protruding fin 111h or as conductive printed layers 115 and 117.

For example, the connecting member 111 may be provided as the via hole 111e in the housing 101 to electrically connect the electrodes 113 with the circuit board 19 (refer to FIG. 15). The via hole 111e may be provided at a position corresponding to the position of installation of the electrodes 113. When the first cover member 201 covers the front surface of the housing 101, the electrodes 113 arranged in the first cover member 201 may be electrically connected with the via hole 111e, and thus, the electrodes 113 may be provided to connect with the circuit board 19 via the via hole 111e. Here, the via hole 111e may be connected with the circuit board 19 directly or via a wire 112 or flexible circuit board 19.

Further, the connecting member 111 may be provided as the protruding fin 111h protruding to the housing 101 in the first cover member 201 to electrically connect the electrodes 113 with the circuit board 19 (refer to FIG. 21). When the first cover member 201 covers the front surface of the housing 101, the protruding fin 111h is led from the first cover member 201 into the inside of the housing 101 to electrically connect with the circuit board 19 provided inside the housing 101. Here, the protruding fin 111h may be led into the inside of the housing 101 to electrically connect with the circuit board 19 directly or via the wire 112 or conductive material layer 111g. Although not shown, a slit corresponding to the protruding fin 111i may be formed in the housing 101, and the protruding fin 111i may be disposed through the slit into the inside of the housing 101 to connect with the circuit device.

Further, the connecting member 111 may be provided as conductive printed layers 115 and 117 exposed to one surface of the housing 101 to electrically connect the electrodes 113 with the circuit board 19. An end of the conductive printed layer 115 or 117 may be exposed to the surface of the housing 101, and the other end may be connected with the circuit board 19 via the inside of the housing 101. The first cover member 201 may contact the outer surface of the housing 101 while covering one surface of the housing 101. As the electrodes 113 arranged in the first cover member 201 contact the conductive printed layers 115 and 117, the electrodes 113 may be electrically connected with the circuit board 19 via the conductive printed layers 115 and 117. The conductive printed layers 115 and 117 may be formed of the printed layer 117 providing a decorative design of regularly or irregularly repeated patterns or the symbol of manufacturer or carrier.

The electrodes 113 arranged in the first cover member 201 may overlap the input unit 11 depending on the position of the first cover member 201. Although a touch panel is integrated with the input unit 11, the input unit 11 and the touch panel may be turned into a standby mode by closure by the first cover member 201 in the state overlapped by the electrodes 113. Accordingly, the electrodes 113 may detect bio signals without interference with the touch panel. The first cover member 201 may rotate, and in the state where the input unit 11 is opened, the electrodes 113 may perform an independent operation without interference with the input unit 11 or touch panel integrated with the input unit 11. For example, the user may contact his body portion, e.g., a finger, to the electrodes 113 to perform measurement on his bio information while manipulating the portable bio information measuring device 100 using the touch panel integrated with the input unit 11. As such, when there is the first cover member 201 opening and closing the input unit 11, and the electrodes 113 are arranged in the first cover member 201, the electrodes 113 may be arranged at various positions on the first cover member 201. For example, the electrodes 113 may be arranged to or not to overlap the input unit 11.

Figure 35:
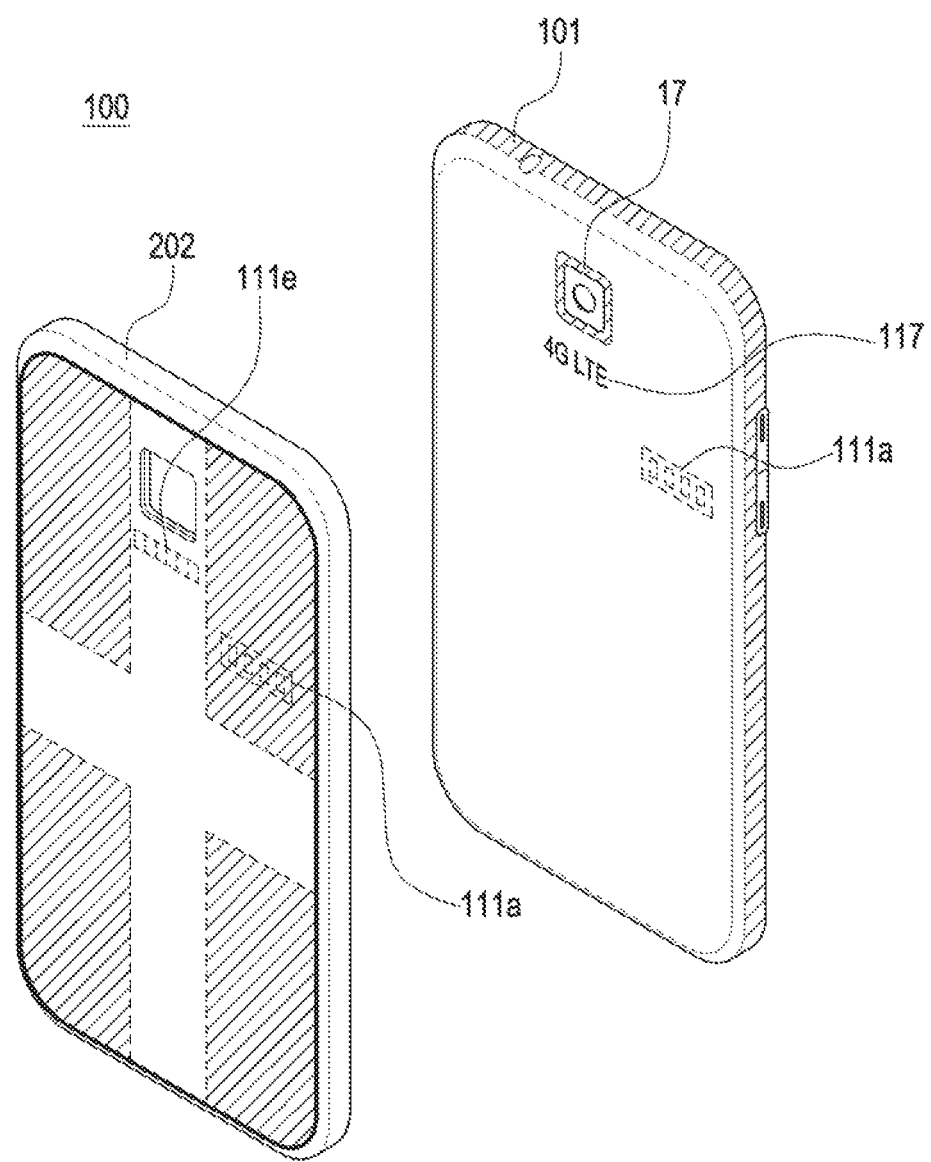
FIG. 35 is a view illustrating an embodiment of a cover unit having electrodes and a connecting member in a portable bio information measuring device according to an embodiment of the present disclosure.

FIG. 35 is a view illustrating an embodiment of a cover unit 200 including electrodes 113 and a connecting member 111 in a portable bio information measuring device 100 according to an embodiment of the present disclosure.

Referring to FIG. 35, the electrodes 113 may be provided on the outer surface of the second cover member 202, and the electrodes 113 may be arranged on an entire surface of the second cover member 202 or at a predetermined position.

The connecting member 111 may be provided as the via hole 111e, as the protruding fin 111h, or as including at least one of conductive printed layers 115 and 117 or a connecting terminal.

For example, the connecting member 111 may be provided as the via hole 111e in the housing 101 to electrically connect the electrodes 113 with the circuit board 19. The via hole 111e may be provided at a position corresponding to the position of installation of the electrodes 113. Further, the second cover member 202 may include a connecting pad P to engage with the via hole 111e. When the second cover member 202 covers the rear surface of the housing 101, the electrodes 113 arranged in the second cover member 202 may be electrically connected with the via hole 111e via the connecting pad P, and thus, the electrodes 113 may be provided to connect with the circuit board 19 via the via hole 111e. Here, the via hole 111e may be connected with the circuit board 19 directly or via a wire 112 or flexible circuit board 19.

Further, the connecting member 111 may be provided as the protruding fin 111h protruding to the rear surface of the housing 101 in the second cover member 202 to electrically connect the electrodes 113 with the circuit board 19. When the second cover member 202 covers the rear surface of the housing 101, the protruding fin 111h is led from the second cover member 202 into the inside of the housing 101 to electrically connect with the circuit board 19 provided inside the housing 101. Here, the protruding fin 111h may be led into the inside of the housing 101 to electrically connect with the circuit board 19 directly or via the wire 112 or conductive material layer 111g. Although not shown, a slit corresponding to the protruding fin 111i may be formed in the housing 101, and the protruding fin 111i may be disposed through the slit into the inside of the housing 101 to connect with the circuit device.

Further, the connecting member 111 may be provided as conductive printed layers 115 and 117 exposed to one surface of the housing 101 to electrically connect the electrodes 113 with the circuit board 19. An end of the conductive printed layer 115 or 117 may be exposed to the surface of the housing 101, and the other end may be connected with the circuit board 19 via the inside of the housing 101. Further, the connecting pad P may be provided on an inner surface of the second cover member 202 to connect with the conductive printed layers 115 and 117. The second cover member 202 may contact the rear surface of the housing 101 while covering one surface of the housing 101. As the connecting pad disposed in the second cover member 202 contacts the conductive printed layers 115 and 117, the electrodes 113 may be electrically connected with the circuit board 19 via the conductive printed layers 115 and 117. The conductive printed layers 115 and 117 may be formed of the printed layer 117 providing a decorative design of regularly or irregularly repeated patterns or the symbol of manufacturer or carrier.

Further, the connecting member 111 may be provided as the connecting terminals 111a and 111b to electrically connect the electrodes 113 with the circuit board 19. The connecting terminals 111a and 111b may include a first electrode 111a disposed in the resonance of the housing 101 and a second terminal 111b (connecting pad P) provided in an inner surface of the second cover member 202 and electrically connecting with the electrodes 113. An end of the connecting terminal 111a or 111b, e.g., the first terminal 111a, may be exposed to the rear surface of the housing 101, and the other end may be connected with the circuit board 19 via the inside of the housing 101. When the second cover member 202 covers the rear surface of the housing 101, the second cover member 202 may contact the rear surface of the housing 10, and the first terminal 111a and the second terminal 111b may be electrically connected. As the first terminal 111a and the second terminal 111b are electrically connected, the electrodes 113 may be electrically connected with the circuit board 19 via the first terminal 111a and the second terminal 111b. The connecting terminal may be implemented as a C-clip or pogo pin.

Hereinafter, an example in which the electrodes 113 are provided in at least one of the first cover part 201 or the second cover part 202 of the third cover member 200 is described with reference to FIGS. 36 to 40.

Figure 36A:
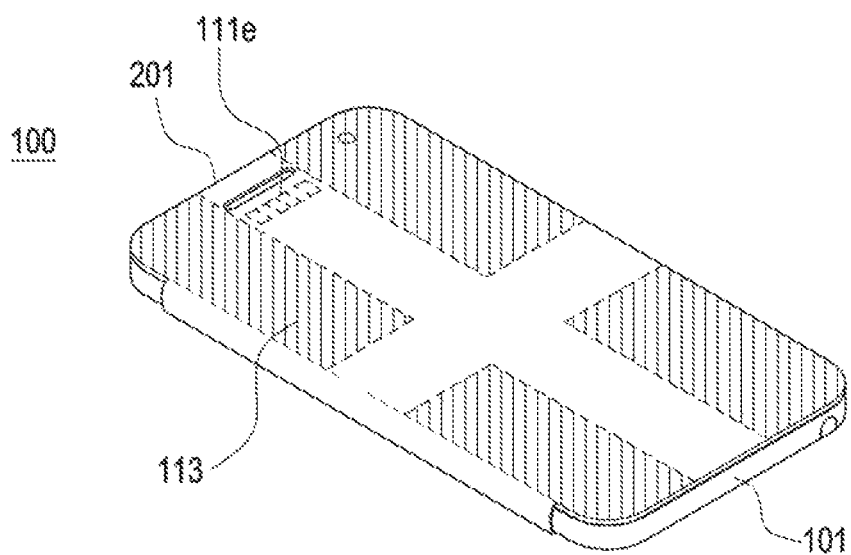
FIGS. 36A and 36B are views illustrating an embodiment of a cover unit having electrodes and a connecting member in a portable bio information measuring device, wherein an electrode portion is provided in a first cover unit, according to various embodiments of the present disclosure.
Figure 36B:
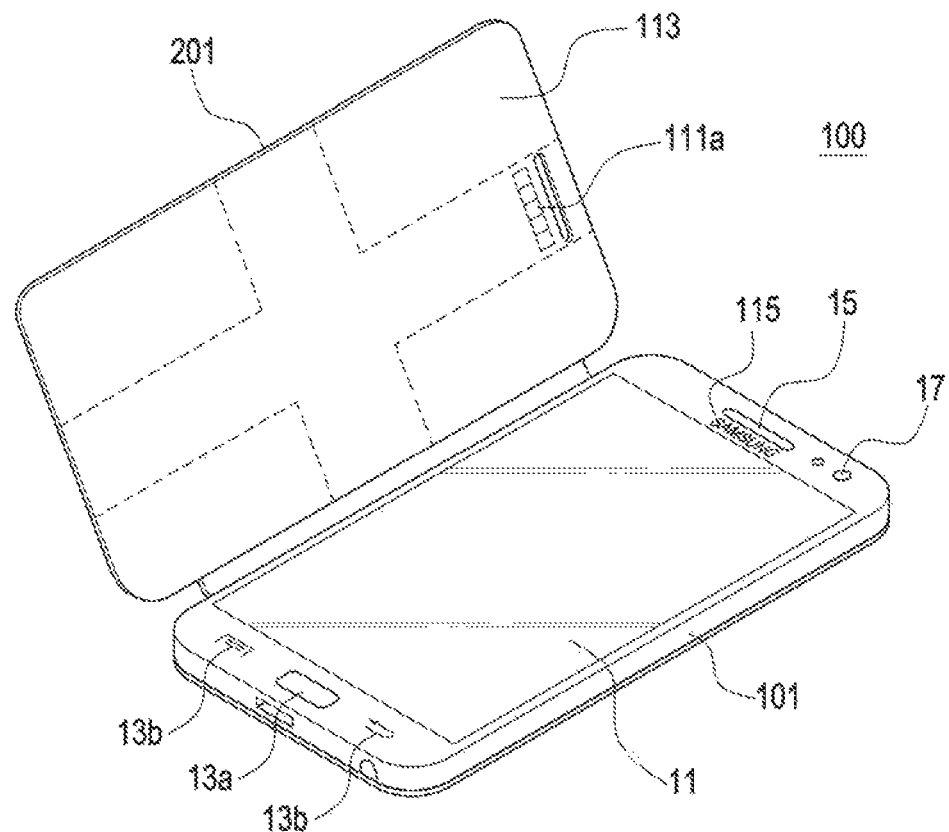
Figure 37A:
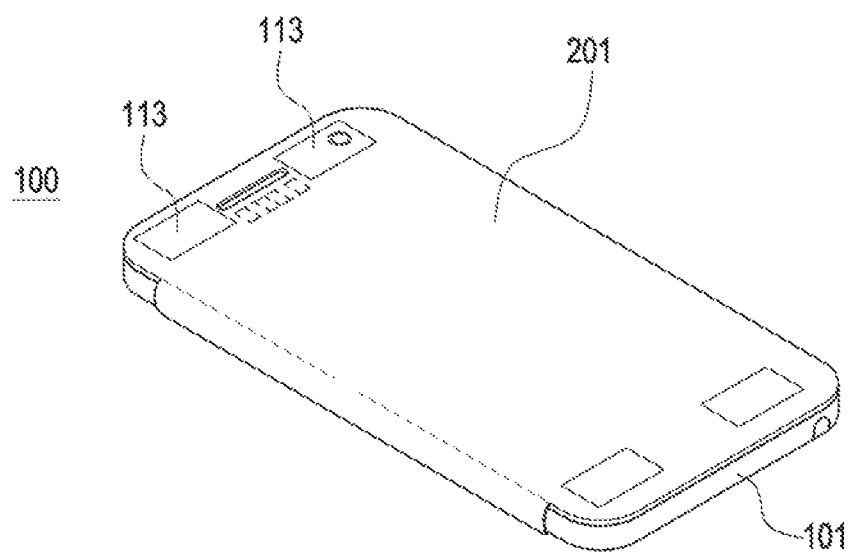
FIGS. 37A and 37B are views illustrating an embodiment of a cover unit having electrodes and a connecting member in a portable bio information measuring device, wherein an electrode portion is provided in a different shape in a first cover unit, according to various embodiments of the present disclosure.
Figure 37B:
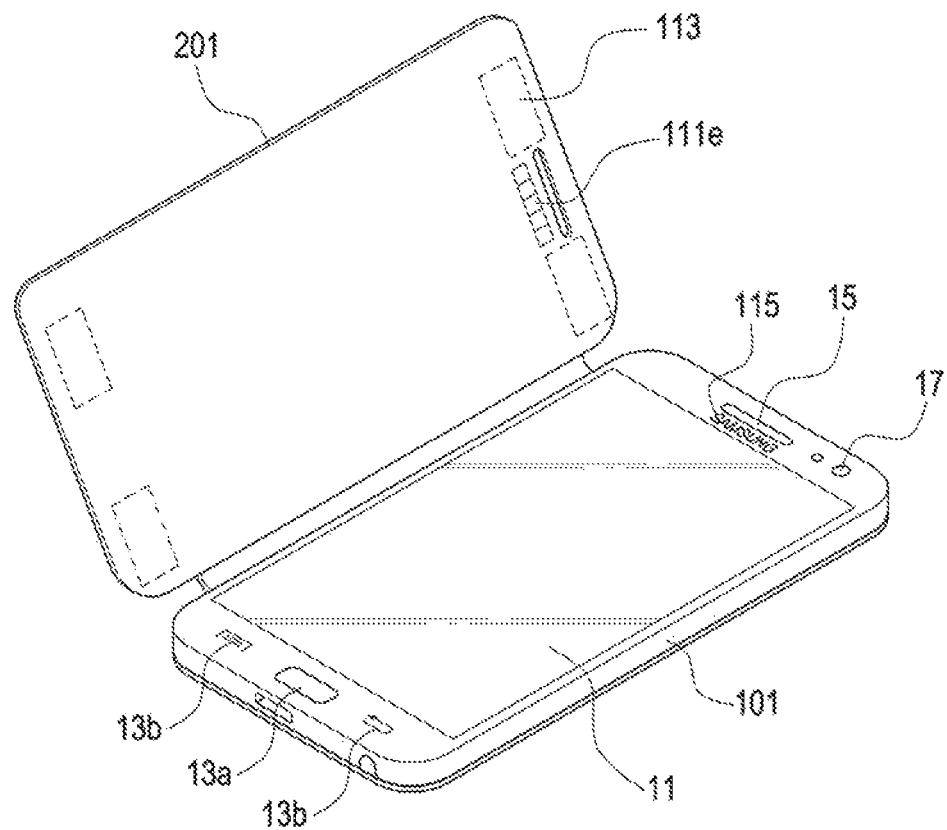

FIGS. 36A and 36B are views illustrating an embodiment of a cover unit 200 including electrodes 113 and the connecting member 111 in a portable bio information measuring device 100 according to various embodiments of the present disclosure. FIGS. 37A and 37B are views illustrating an embodiment of a cover unit 200 including electrodes 113 and the connecting member 111 in a portable bio information measuring device 100 according to various embodiments of the present disclosure.

Referring to FIGS. 36A to and 37B, the electrodes 113 may be provided on the outer surface of the first cover part 201. When the second cover part 202 is coupled while covering the rear surface of the housing 101, the first cover part 201 is rotated on the second cover part 202 to cover the front surface of the housing 101.

The electrodes 113 may be provided on the outer surface of the first cover part 201, and the electrodes 113 may be arranged in an entire surface of the first cover part 201 or at, at least one, of positions corresponding to a surrounding edge of the input unit 11.

When the electrodes 113 are arranged in the entire surface of the first cover part 201 or at, at least, one of the positions corresponding to the surrounding edge of the input unit 11, the connecting member 111 may be provided as the via hole 111e, or alternately, may be provided as a protruding fin 111h or as conductive printed layers 115 and 117. Further, the electrodes 113 may be provided on the outer surface of the first cover part 201, and the connecting member 111 electrically connecting the electrodes 113 with the circuit board 19 inside the housing 101 may be disposed in the second cover part 202.

For example, the connecting member 111 may be provided as the via hole 111e in the housing 101 to electrically connect the electrodes 113 with the circuit board 19 (refer to FIG. 15). The via hole 111e may be provided at a position corresponding to the position of installation of the electrodes 113. When the first cover part 201 covers the front surface of the housing 101, the electrodes 113 arranged in the first cover part 201 may be electrically connected with the via hole 111e, and thus, the electrodes 113 may be provided to connect with the circuit board 19 via the via hole 111e. Here, the via hole 111e may be connected with the circuit board 19 directly or via a wire 112 or flexible circuit board 19.

Further, the connecting member 111 may be provided as the protruding fin 111h protruding to the housing 101 in the first cover part 201 to electrically connect the electrodes 113 with the circuit board 19 (refer to FIG. 21). When the first cover part 201 covers the front surface of the housing 101, the protruding fin 111h is led from the first cover part 201 into the inside of the housing 101 to electrically connect with the circuit board 19 provided inside the housing 101. Here, the protruding fin 111h may be led into the inside of the housing 101 to electrically connect with the circuit board 19 directly or via the wire 112 or conductive material layer 111g. Although not shown, a slit corresponding to the protruding fin 111i may be formed in the housing 101, and the protruding fin 111i may be disposed through the slit into the inside of the housing 101 to connect with the circuit board 19.

Further, the connecting member 111 may be provided as conductive printed layers 115 and 117 exposed to one surface of the housing 101 to electrically connect the electrodes 113 with the circuit board 19. An end of the conductive printed layer 115 or 117 may be exposed to the surface of the housing 101, and the other end may be connected with the circuit board 19 via the inside of the housing 101. The first cover part 201 may contact the outer surface of the housing 101 while covering one surface of the housing 101. As the electrodes 113 arranged in the first cover part 201 contact the conductive printed layers 115 and 117, the electrodes 113 may be electrically connected with the circuit board 19 via the conductive printed layers 115 and 117. The conductive printed layers 115 and 117 may be formed of the printed layer 117 providing a decorative design of regularly or irregularly repeated patterns or the symbol of manufacturer or carrier.

The electrodes 113 may be provided on the outer surface of the first cover part 201, and the connecting member 111 electrically connecting the electrodes 113 with the circuit board 19 inside the housing 101 may be disposed in the second cover part 202. For example, the connecting member 111 may be provided as the via hole 111e on the rear surface of the housing 101, as the protruding fin 111h protruding from the second cover part 202, as the conductive printed layers 115 and 117 on the rear surface of the housing 101, or as including at least one of the connecting terminals.

Figure 38:
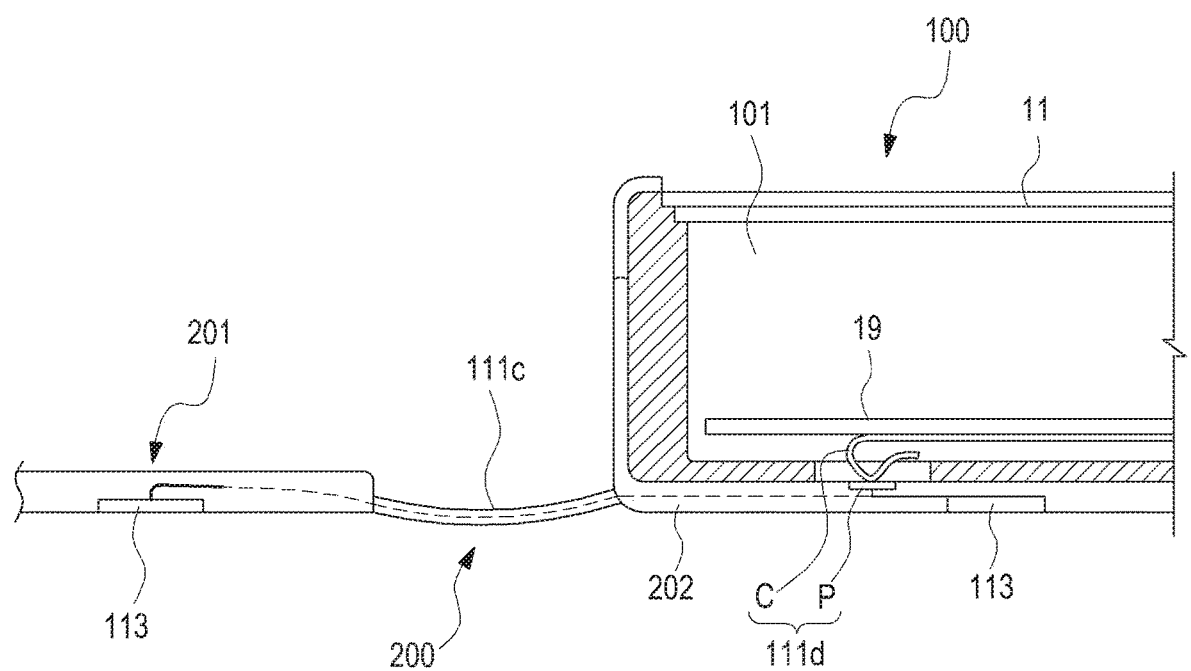
FIG. 38 is a view illustrating a different shape of a connecting member in an embodiment of a cover unit having electrodes and a connecting member in a portable bio information measuring device, according to an embodiment of the present disclosure.

FIG. 38 is a view illustrating an embodiment of a cover unit 200 including electrodes 113 and a connecting member 111 in a portable bio information measuring device 100 according to an embodiment of the present disclosure, wherein the connecting member 111 has a different shape.

Referring to FIG. 38, the connecting member 111 may include a first connecting part 111c provided in contacting surfaces where the housing 101 faces the second cover part 202 to electrically connect the housing 101 with the cover part 20 and a second connecting part 111d provided between the electrodes 113 and the first connecting part 111c to electrically connect the electrodes 113 with the first connecting part 111c.

The first connecting part 111c may be formed as a connecting line electrically connect the electrodes 113 with the second connecting part 111d. The second connecting part 111d may be provided as the via hole 111e on the rear surface of the housing 101, as the protruding fin 111h protruding from the second cover part 202, as the conductive printed layers 115 and 117 on the rear surface of the housing 101, or as including at least one of the connecting terminals.

For example, the second connecting part 111d may be provided as the via hole 111e on the rear surface in the housing 101 to electrically connect the electrodes 113 with the circuit board 19. When the second cover part 202 covers the rear surface of the housing 101, the housing 101 and the second cover part 202 may be electrically connected through the second connecting part 111d. Accordingly, the electrodes 113 may be connected with the circuit board 19 via the connecting line and the via hole 111e. Here, the via hole 111e may be connected with the circuit board 19 directly or via a wire 112 or flexible circuit board 19.

Further, the second connecting part 111d may be provided as the protruding fin 111h protruding from the second cover part 202 to the rear surface side of the housing 101. When the second cover part 202 covers the rear surface of the housing 101, the protruding fin 111h is led from the second cover member 202 into the inside of the housing 101 to electrically connect with the circuit board 19 provided inside the housing 101. Here, the protruding fin may be led into the inside of the housing 101 to electrically connect with the circuit board 19 directly or via the wire 112 or conductive material layer 111g. Although not shown, a slit corresponding to the protruding fin 111i may be formed in the housing 101, and the protruding fin 111i may be disposed through the slit into the inside of the housing 101 to connect with the circuit device. Accordingly, the electrodes 113 arranged in the first cover part 201 may be connected with the circuit board 19 via the connecting line and the protruding fin 111h.

Further, the second connecting part 111d may be provided as conductive printed layers 115 and 117 exposed to the rear surface of the housing 101. An end of the conductive printed layer 115 or 117 may be exposed to the rear surface of the housing 101, and the other end may be connected with the circuit board 19 via the inside of the housing 101. As the second cover part 202 covers a surface of the housing 101, the second cover part 202 may come in contact with the rear surface of the housing 101. The second cover part 202 may be electrically connected with the housing 101 through the conductive printed layers 115 and 117. The conductive printed layers 115 and 117 may be formed of the printed layer 117 providing a decorative design of regularly or irregularly repeated patterns or the symbol of manufacturer or carrier. Accordingly, the electrodes 113 may be connected with the circuit board 19 via the connecting line and the protruding fin 111h.

Further, a second connecting part 111d may be provided as connecting terminals 111a and 111b to electrically connect the electrodes 113 with the circuit board 19. The second connecting part 111d may include the first electrode 111a disposed in the resonance of the housing 101 and the second terminal 111b provided in an inner surface of the second cover member 202 and electrically connecting with the electrodes 113. An end of the connecting terminal, e.g., the first terminal 111a, may be exposed to the rear surface of the housing 101, and the other end may be connected with the circuit board 19 via the inside of the housing 101. When the second cover part 202 covers the rear surface of the housing 101, the second cover part 202 may contact the rear surface of the housing 10, and the first terminal 111a and the second terminal 111b may be electrically connected. As the first terminal 111a and the second terminal 111b are electrically connected, the electrodes 113 may be electrically connected with the circuit board 19 via the connecting line, the first terminal 111a and the second terminal 111b. The connecting terminal may be implemented as a C-clip or pogo pin.

Figure 39:
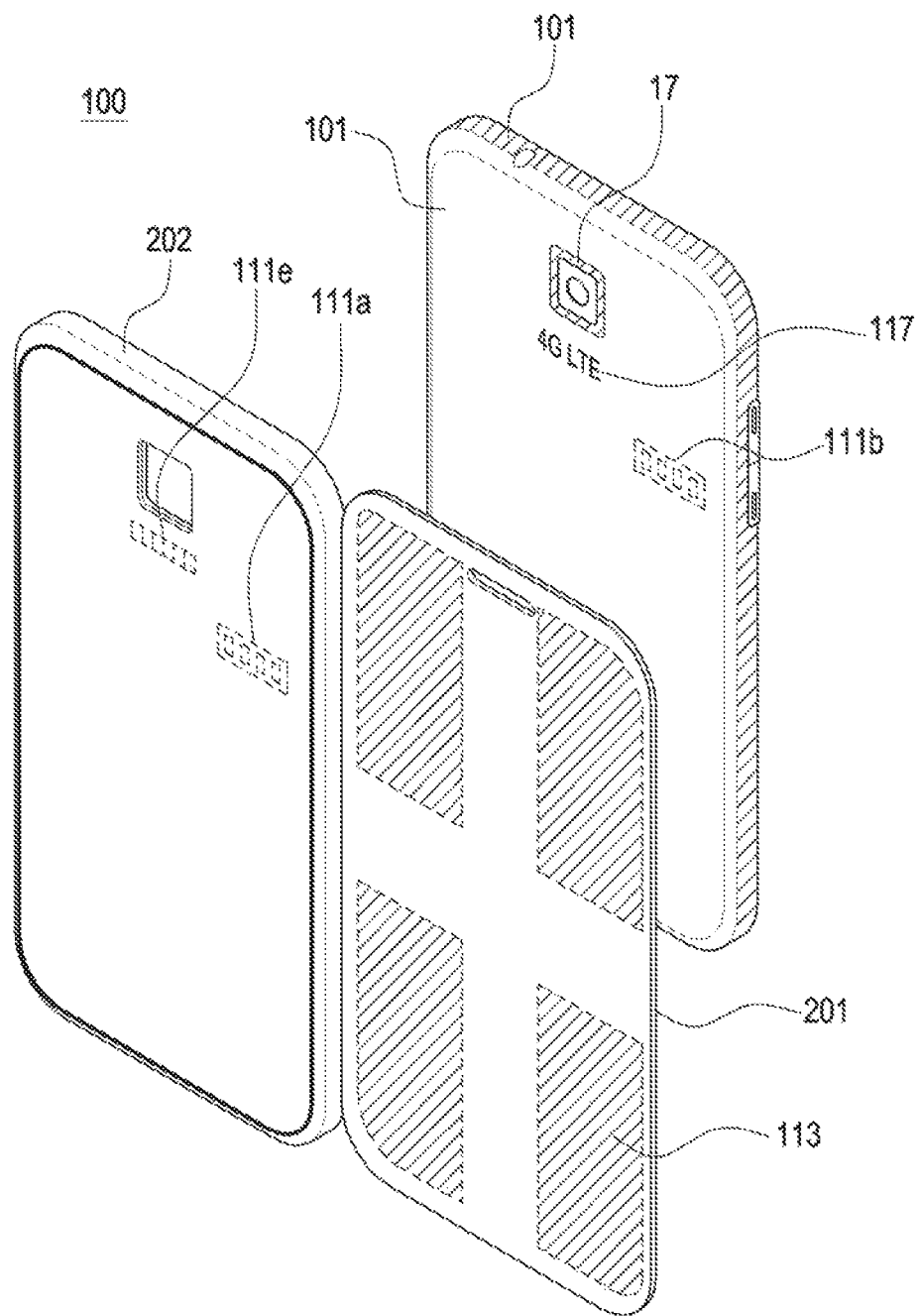
FIG. 39 is a view illustrating an embodiment of a cover unit having electrodes and a connecting member in a portable bio information measuring device, wherein an electrode portion is provided in a first cover unit, according to an embodiment of the present disclosure.
Figure 40:
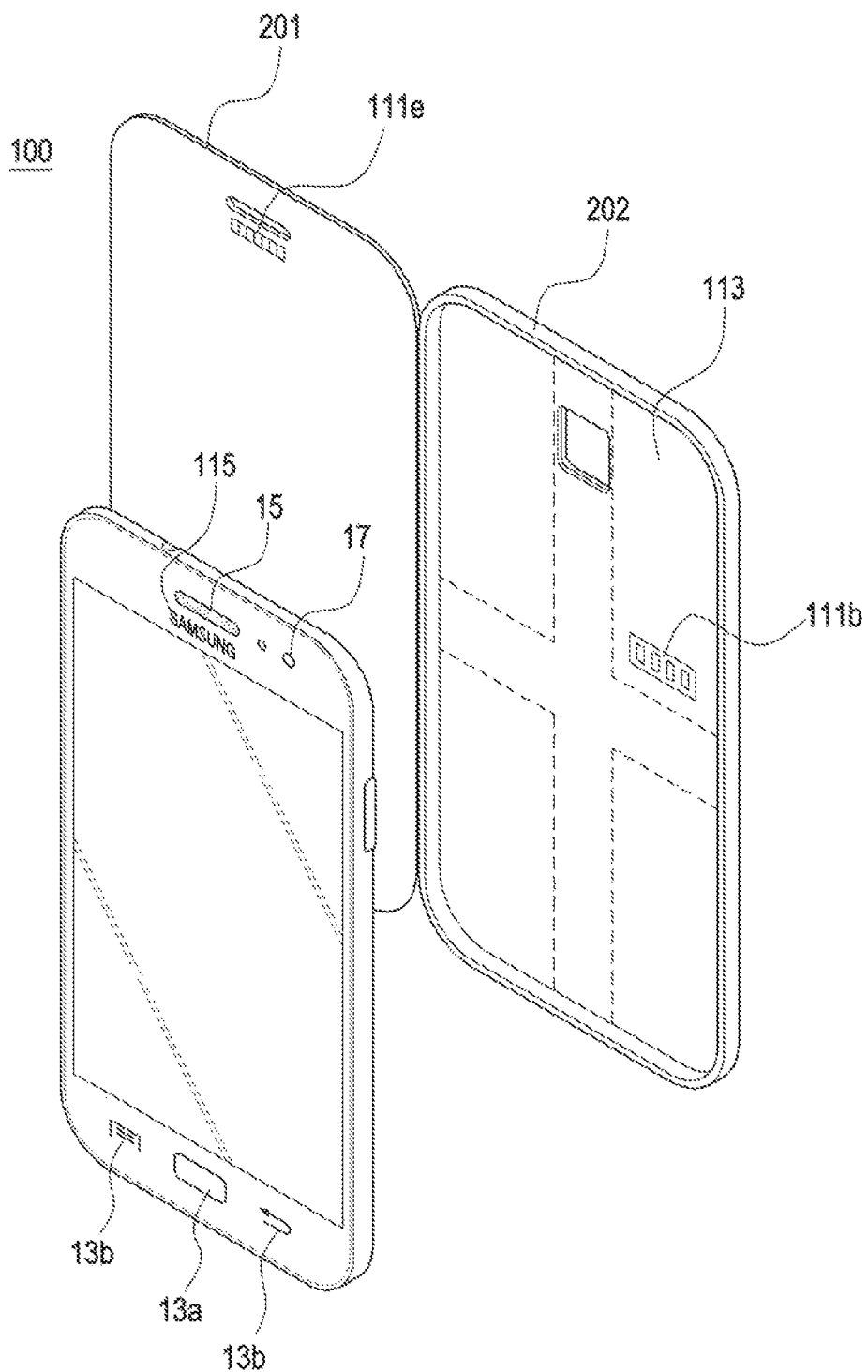
FIG. 40 is a view illustrating an embodiment of a cover unit having electrodes and a connecting member in a portable bio information measuring device, wherein an electrode portion is provided in a different shape in a first cover unit, according to an embodiment of the present disclosure.

FIG. 39 is a view illustrating an embodiment of a cover unit 200 including electrodes 113 and a connecting member 111 in a portable bio information measuring device 100 according to an embodiment of the present disclosure, wherein an electrode part is provided in the first cover part 201. FIG. 40 is a view illustrating an embodiment of a cover unit 200 including electrodes 113 and a connecting member 111 in a portable bio information measuring device 100 according to an embodiment of the present disclosure, wherein an electrode part is provided in a different form in the first cover part 201.

Referring to FIGS. 39 and 40, the electrodes 113 may be provided on the outer surface of the second cover part 202, and the electrodes 113 may be arranged on an entire surface of the second cover part 202 or at a predetermined position.

The connecting member 111 may be provided as the via hole 111e, as a protruding fin 111h, or as including at least one of conductive printed layers 115 and 117 or a connecting terminal.

For example, the connecting member 111 may be provided as the via hole 111e in the housing 101 to electrically connect the electrodes 113 with the circuit board 19. The via hole 111e may be provided at a position corresponding to the position of installation of the electrodes 113. Further, the second cover part 202 may include a connection pad P to engage with the via hole 111e. When the second cover part 202 covers the rear surface of the housing 101, the electrodes 113 arranged in the second cover part 202 may be electrically connected with the via hole 111e via the connection pad P, and thus, the electrodes 113 may be provided to connect with the circuit board 19 via the via hole 111e. Here, the via hole 111e may be connected with the circuit board 19 directly or via a wire 112 or flexible circuit board 19.

Further, the connecting member 111 may be provided as the protruding fin 111h protruding to the rear surface of the housing 101 in the second cover part 202 to electrically connect the electrodes 113 with the circuit board 19. When the second cover part 202 covers the rear surface of the housing 101, the protruding fin 111h is led from the second cover part 202 into the inside of the housing 101 to electrically connect with the circuit board 19 provided inside the housing 101. Here, the protruding fin 111h may be led into the inside of the housing 101 to electrically connect with the circuit board 19 directly or via the wire 112 or conductive material layer 111g. Although not shown, a slit corresponding to the protruding fin 111i may be formed in the housing 101, and the protruding fin 111i may be disposed through the slit into the inside of the housing 101 to connect with the circuit device.

Further, the connecting member 111 may be provided as conductive printed layers 115 and 117 exposed to one surface of the housing 101 to electrically connect the electrodes 113 with the circuit board 19. An end of the conductive printed layer 115 or 117 may be exposed to the surface of the housing 101, and the other end may be connected with the circuit board 19 via the inside of the housing 101. Further, the connecting pad P may be provided on an inner surface of the second cover part 202 to connect with the conductive printed layers 115 and 117. The second cover part 202 may contact the rear surface of the housing 101 while covering one surface of the housing 101. As the connecting pad disposed in the second cover part 202 contacts the conductive printed layers 115 and 117, the electrodes 113 may be electrically connected with the circuit board 19 via the conductive printed layers 115 and 117. The conductive printed layers 115 and 117 may be formed of the printed layer 117 providing a decorative design of regularly or irregularly repeated patterns or the symbol of manufacturer or carrier.

Further, the connecting member 111 may be provided as connecting terminals 111a and 111b to electrically connect the electrodes 113 with the circuit board 19. The connecting terminals 111a and 111b may include the first electrode 111a disposed in the resonance of the housing 101 and the second terminal 111b (connecting pad P) provided in an inner surface of the second cover part 202 and electrically connecting with the electrodes 113. An end of the connecting terminal 111a or 111b, e.g., the first terminal 111a, may be exposed to the rear surface of the housing 101, and the other end may be connected with the circuit board 19 via the inside of the housing 101. When the second cover part 202 covers the rear surface of the housing 101, the second cover part 202 may contact the rear surface of the housing 10, and the first terminal 111a and the second terminal 111b may be electrically connected. As the first terminal 111a and the second terminal 111b are electrically connected, the electrodes 113 may be electrically connected with the circuit board 19 via the first terminal 111a and the second terminal 111b. The connecting terminal may be implemented as a C-clip or pogo pin.

As is apparent from the foregoing description, according to an embodiment of the present disclosure, the portable bio information measuring device may include the transparent electrodes or conductive printed electrodes for detecting the user's bio signals in an outer surface except the input unit provided in the electronic device (e.g., the housing), e.g., around the input unit or on the rear surface of the housing 101. Thus, the electrodes may detect bio signals through the portable bio information measuring device, and the electrodes may be placed in a harmonized manner with the design of housing without influencing the design of the housing.

According to an embodiment of the present disclosure, the portable bio information measuring device may utilize the outer metallic decoration or design as electrodes for detecting the user's bio signals or as a connecting member for connecting with the circuit board without deteriorating the elegant design of the electronic device. Thus, the housing may remain in an elegant design while functioning as an electrode for detecting bio signals. Further, the conductive decorations, such as regular or irregular patterns, characters, or drawings on the appearance of the housing may be utilized as electrodes or connecting members for connection of electrodes. Thus, the conductive decorations may have diversified uses, and the electronic device may remain elegant.

According to an embodiment of the present disclosure, in the portable bio information measuring device, the electrodes are arranged on the appearance thereof, which are configured as layers easy to contact with the user's body and contribute to the miniaturization of the electronic device while eliminating the need for an additional space for installation inside the electronic device.

According to an embodiment of the present disclosure, the portable bio information measuring device may be provided on the outer surface of the covering device covering the electronic device, e.g., a terminal. Thus, a portable bio information measuring device need not be separately installed inside the electronic device and may be implemented together with other parts in the electronic device without additional space for installation in the electronic device.

While the inventive concept has been shown and described with reference to various embodiments thereof, it will be apparent to those of ordinary skill in the art that various changes in form and detail may be made thereto without departing from the spirit and scope of the inventive concept as defined by the following claims. For example, in the above-described embodiments, although the connecting member is exemplified as the indium tin oxide, conductive mesh, silver nano, or graphene, various electrically connecting structures including wiring, a printed circuit pattern, flexible printed circuit board, or via holes, may be utilized to connect the electrodes to the circuit device (e.g., the circuit board) of the electronic device.

What is claimed is:

1. A portable bio information measuring device, comprising:
    a circuit board positioned in the portable bio information measuring device;
    a housing accommodating the circuit board and including a front surface and a rear surface, at least one of the front surface or the rear surface comprising a plurality of electrodes and a connecting member disposed continuously therethrough between the plurality of electrodes and wherein the plurality of electrodes and the connecting member form the at least one of the front surface or the rear surface of the housing;
    the plurality of electrodes configured to form a first portion of the rear surface of the housing,
        wherein the plurality of electrodes comprise at least one of a transparent electrode, a conductive decoration, or a conductive printed electrode, and
        wherein the plurality of electrodes are configured to measure bio information;
    the connecting member configured to:
        form a second portion of the rear surface of the housing between the plurality of electrodes, and
        electrically and directly connect the circuit board with the plurality of electrodes inside the housing; and
    a display device, disposed at the front surface of the housing, comprising a display unit and a touch panel, wherein the plurality of electrodes are disposed in different positions with respect to the display device so that interference with the display device is prevented, and
    wherein the connecting member comprises a via hole passing between the plurality of electrodes and the circuit board in the portable bio information measuring device.

2. The portable bio information measuring device of claim 1,
    wherein a portion of the conductive decoration is formed as the connecting member connected with the circuit board, and
    wherein the plurality of electrodes are provided to be connected with the circuit board through the conductive decoration.

3. The portable bio information measuring device of claim 2, wherein the conductive decoration is configured to be electrically connected with the circuit board directly or using at least one of a wire, a via hole, or an electrical connecting part.

4. The portable bio information measuring device of claim 1, wherein the conductive decoration comprises at least one of a conductive printed layer, a frame disposed around a module exposed to an outer surface of the housing, or a side frame provided in an edge of the housing.

5. The portable bio information measuring device of claim 1, wherein the connecting member comprises at least one of a conductive ink, a flexible printed circuit board, or a conductive mesh.

6. The portable bio information measuring device of claim 1, further comprising:
    a base substrate comprising glass or a synthetic resin provided on at least one surface of the housing; and
    a wiring layer positioned over a side surface of an outer circumference of the base substrate,
    wherein the plurality of electrodes are formed on the wiring layer over the outer circumference of the base substrate.

7. The portable bio information measuring device of claim 6,
    wherein the wiring layer comprises a conductive mesh or silver nano material, and
    wherein the plurality of electrodes comprise at least one of indium tin oxide (ITO), conductive mesh, silver nano, or graphene material.

8. The portable bio information measuring device of claim 6,
    wherein a portion of the wiring layer is formed of the connecting member connected with the circuit board.

9. A portable bio information measuring device, comprising:
    a circuit board;
    a housing accommodating the circuit board and including a front surface and a rear surface, at least one of the front surface or the rear surface comprising a plurality of electrodes and a connecting member disposed continuously therethrough between the plurality of electrodes and wherein the plurality of electrodes and the connecting member form the at least one of the front surface or the rear surface of the housing;
    the plurality of electrodes configured to form a first portion of the rear surface of the housing;
    a base substrate positioned on at least one of the rear surface of the housing or the front surface of the housing;
    the connecting member configured to:

form a second portion of the rear surface of the housing between the plurality of electrodes, and electrically and directly connect the circuit board with the plurality of electrodes inside the housing; and a display device, disposed at the front surface of the housing, comprising a display unit and a touch panel, wherein the plurality of electrodes are disposed in different positions with the display device so that interference with the display device is prevented, wherein the base substrate is configured to partially or fully house the plurality of electrodes, wherein the plurality of electrodes are configured to measure bio information when a user contacts the base substrate, and wherein the connecting member comprises a via hole passing between the plurality of electrodes and the circuit board in the portable bio information measuring device.

* * * * *